(12) United States Patent
Kuhn et al.

(10) Patent No.: US 12,285,576 B2
(45) Date of Patent: Apr. 29, 2025

(54) METHODS AND SYSTEMS FOR TRANSCAVAL TREATMENT OF ANEURYSMS

(71) Applicant: Texas Medical Center, Houston, TX (US)

(72) Inventors: Matthew Kuhn, Houston, TX (US); Melanie Lowther, Houston, TX (US)

(73) Assignee: Texas Medical Center, Houston, TX (US)

( * ) Notice: Subject to any disclaimer, the term of this patent is extended or adjusted under 35 U.S.C. 154(b) by 0 days.

(21) Appl. No.: 18/634,734

(22) Filed: Apr. 12, 2024

(65) Prior Publication Data

US 2024/0252793 A1 Aug. 1, 2024

Related U.S. Application Data

(63) Continuation of application No. PCT/US2024/012436, filed on Jan. 22, 2024.
(Continued)

(51) Int. Cl.
*A61M 27/00* (2006.01)
*A61B 17/11* (2006.01)
(Continued)

(52) U.S. Cl.
CPC ........... *A61M 27/002* (2013.01); *A61B 17/11* (2013.01); *A61B 17/12113* (2013.01); *A61F 2/064* (2013.01); *A61F 2/07* (2013.01); *A61B 2017/1107* (2013.01); *A61B 2017/1139* (2013.01); *A61F 2002/061* (2013.01);
(Continued)

(58) Field of Classification Search
CPC ............ A61M 27/002; A61M 2205/04; A61M 2205/3331; A61M 22/127; A61B 17/11
See application file for complete search history.

(56) References Cited

U.S. PATENT DOCUMENTS

| 6,068,638 A | 5/2000 | Makower |
| 6,287,317 B1 | 9/2001 | Makower et al. |

(Continued)

FOREIGN PATENT DOCUMENTS

| WO | WO-2020232384 A1 | 11/2020 |
| WO | WO-2024155994 A1 | 7/2024 |

OTHER PUBLICATIONS

PCT/US2024/012436 International Search Report and Written Opinion mailed Jun. 13, 2024.

*Primary Examiner* — Leslie R Deak
(74) *Attorney, Agent, or Firm* — Goodwin Procter LLP

(57) ABSTRACT

Described herein, in some aspects, are systems and methods for treating aortic aneurysms. In some embodiments, a method of treating an aortic aneurysm in a subject comprises: advancing a shunt through a venous puncture site of a vein to access an arterial puncture site of an artery, the arterial puncture site disposed within the aortic aneurysm or upstream of the aortic aneurysm; and securing the shunt to the artery and vein by deploying i) an arterial sealing structure coupled to a distal end of the shunt, and ii) deploying a venous sealing structure coupled to a proximal end of the shunt, thereby enabling fluid to flow from the artery to the vein. In some embodiments, a method of treating an aortic aneurysm in a subject comprises: implanting a graft within a subject to at least partially bypass a fluid flow through an artery around the aortic aneurysm, the graft having a lumen therein.

30 Claims, 28 Drawing Sheets

Related U.S. Application Data

(60) Provisional application No. 63/480,924, filed on Jan. 20, 2023.

(51) Int. Cl.
*A61B 17/12* (2006.01)
*A61F 2/06* (2013.01)
*A61F 2/07* (2013.01)
*A61F 2/82* (2013.01)

(52) U.S. Cl.
CPC ... *A61F 2002/068* (2013.01); *A61F 2002/823* (2013.01); *A61F 2210/0014* (2013.01); *A61M 2205/0216* (2013.01); *A61M 2205/0266* (2013.01); *A61M 2209/088* (2013.01); *A61M 2210/127* (2013.01)

(56) References Cited

U.S. PATENT DOCUMENTS

| | | | |
|---|---|---|---|
| 6,464,665 B1 | 10/2002 | Heuser | |
| 6,485,513 B1 | 11/2002 | Fan | |
| 7,374,567 B2 | 5/2008 | Heuser | |
| 7,828,814 B2 | 11/2010 | Brenneman et al. | |
| 7,967,769 B2 | 6/2011 | Faul et al. | |
| 8,016,782 B2 | 9/2011 | Brenneman et al. | |
| 8,043,360 B2 | 10/2011 | McNamara et al. | |
| 8,157,860 B2 | 4/2012 | McNamara et al. | |
| 8,172,896 B2 | 5/2012 | McNamara et al. | |
| 8,235,933 B2 | 8/2012 | Keren et al. | |
| 8,252,042 B2 | 8/2012 | McNamara et al. | |
| 8,273,095 B2 | 9/2012 | Brenneman et al. | |
| 8,460,372 B2 | 6/2013 | McNamara et al. | |
| 8,641,724 B2 | 2/2014 | Brenneman et al. | |
| 8,926,545 B2 | 1/2015 | Brenneman et al. | |
| 8,932,341 B2 | 1/2015 | Brenneman | |
| 9,011,362 B2 | 4/2015 | Brenneman et al. | |
| 9,034,034 B2 | 5/2015 | Nitzan et al. | |
| 9,067,050 B2 | 6/2015 | Gallagher et al. | |
| 9,259,340 B2 | 2/2016 | Heuser et al. | |
| 9,301,830 B2 | 4/2016 | Heuser et al. | |
| 9,314,329 B2 | 4/2016 | Dickinson et al. | |
| 9,358,371 B2 | 6/2016 | McNamara et al. | |
| 9,468,441 B2 | 10/2016 | Brenneman | |
| 9,550,022 B2 | 1/2017 | Brenneman et al. | |
| 9,757,107 B2 | 9/2017 | McNamara et al. | |
| 9,775,636 B2 | 10/2017 | Fazio et al. | |
| 9,789,294 B2 | 10/2017 | Taft et al. | |
| 9,820,745 B2 | 11/2017 | Brenneman et al. | |
| 9,937,036 B2 | 4/2018 | Sugimoto et al. | |
| 10,045,765 B2 | 8/2018 | Rafiee et al. | |
| 10,111,998 B2 | 10/2018 | Brenneman et al. | |
| 10,232,098 B2 | 3/2019 | Brenneman et al. | |
| 10,376,680 B2 | 8/2019 | McNamara et al. | |
| 10,398,421 B2 | 9/2019 | Celermajer | |
| 10,463,477 B2 | 11/2019 | Forcucci et al. | |
| 10,568,751 B2 | 2/2020 | McNamara | |
| 10,595,999 B2 | 3/2020 | Vettukattil et al. | |
| 10,624,621 B2 | 4/2020 | Celermajer | |
| 10,632,292 B2 | 4/2020 | Forcucci et al. | |
| 10,675,450 B2 | 6/2020 | Finch | |
| 10,751,057 B2 | 8/2020 | Brenneman et al. | |
| 10,926,068 B2 | 2/2021 | Narayan et al. | |
| 10,932,786 B2 | 3/2021 | McNamara et al. | |
| 10,993,735 B2 | 5/2021 | Vardi et al. | |
| 11,090,177 B2 | 8/2021 | Reis et al. | |
| 11,135,410 B2 | 10/2021 | Finch et al. | |
| 11,160,961 B2 | 11/2021 | Fahey et al. | |
| 11,253,685 B2 | 2/2022 | Fahey et al. | |
| 11,259,789 B2 | 3/2022 | Rowe et al. | |
| 11,717,429 B2 | 8/2023 | Schwartz et al. | |
| 11,752,314 B2 | 9/2023 | Taft et al. | |
| 2001/0044631 A1 | 11/2001 | Akin et al. | |
| 2006/0247761 A1 | 11/2006 | Greenberg et al. | |
| 2008/0241215 A1 | 10/2008 | Falotico et al. | |
| 2010/0016833 A1 | 1/2010 | Ogle et al. | |
| 2010/0057096 A1 | 3/2010 | Wolf | |
| 2010/0268316 A1 | 10/2010 | Brenneman et al. | |
| 2020/0085600 A1 | 3/2020 | Schwartz et al. | |
| 2021/0275177 A1 | 9/2021 | Binmoeller et al. | |
| 2022/0031327 A1 | 2/2022 | Manash et al. | |
| 2022/0125430 A1 | 4/2022 | Rafiee et al. | |
| 2022/0257904 A1 | 8/2022 | Passman et al. | |
| 2022/0273312 A1 | 9/2022 | Goldsmith | |
| 2023/0329753 A1 | 10/2023 | Chang | |

METHODS AND SYSTEMS FOR TRANSCAVAL TREATMENT OF ANEURYSMS

CROSS-REFERENCE TO RELATED APPLICATIONS

This application is a continuation of International Application No. PCT/US2024/012436 filed on Jan. 22, 2024, which claims priority to, and the benefit of, U.S. Provisional App. No. 63/480,924, filed Jan. 20, 2023, the entirety of each of which are incorporated herein by reference.

BACKGROUND

Tissue defects within blood vessels, such as aneurysms (e.g., aortic aneurysms and brain aneurysms) can lead to pain, stroke, and/or eventual ruptures in the vessel. Aneurysms occur when there is a weakening in the wall of the blood vessel leading to a widening, opening or formation of a cavity within the vessel wall. The opening of such a cavity can be further exasperated by the continual interrogation from blood pooling in the cavity pressurizing the already weakened vessel wall. Such a damaged vessel, which can be age-related, drug or tobacco-induced, resulting from atherosclerosis or in some instances, caused by infection, can result in a vessel rupture leading to life-threatening internal bleeding.

BRIEF SUMMARY

An abdominal aortic aneurysm is an aneurysm in the abdominal portion of the aorta (FIGS. 1A-1B), usually located in or near one or both of the two iliac arteries or near the renal arteries. The aneurysm often arises in the infrarenal portion of the diseased aorta, for example, below the kidneys. The occurrence of aneurysms is not confined to the abdominal region. While abdominal aortic aneurysms are generally the most common, aneurysms in other regions of the aorta or one of its branches are possible. For example, a thoracic aortic aneurysm is an aneurysm in the thoracic portion of the aorta. When left untreated, the aneurysm may rupture, usually causing rapid fatal hemorrhaging. A ruptured abdominal aortic aneurysm is presently the thirteenth leading cause of death in the United States. As depicted in FIGS. 1A-1B, the aortic aneurysm is depicted as having an enlarged area (e.g., aneurysm sac).

Endovascular Aortic Aneurysm Repair (EVAR) is a procedure in which a stent-graft prosthesis (hereinafter endograft) is deployed endovascularly to treat an aneurysm, while leaving the aneurysm sac in place (e.g., see FIG. 2). Endografts have been developed to place exclusion devices within or across an opening or cavity associated with the subject tissue defect to preserve blood flow through the damaged blood vessel (e.g., where the aneurysm sac is located) and prevent blood from further pressurizing the damaged vascular tissue. EVAR may be favored over open surgical repair of aneurysms in order to, for example, shorten operation, intensive care, and total hospital times and lower postoperative morbidity. Although EVAR has become a viable alternative to open repair for a significant percentage of abdominal aortic aneurysm patients, the varying shapes, locations, sizes, and other features associated with an abnormal or unhealthy aorta can prevent proper alignment and/or sealing of the endograft with the vessel wall/tissue. As a result, EVAR requires long-term postoperative surveillance to detect complications such as endoleaks, endograft migration, endograft fracture, and aortic neck dilation. Endoleak remains the most severe complication of EVAR and may result in life-threatening sac enlargement and aneurysm rupture if a patient does not receive imaging on a regular basis to detect possible complications. Endoleak occurs in up to 50% of all EVAR cases. Almost 30% of patients require reintervention within 5 years after EVAR due to endoleaks causing aneurysm sac enlargement.

Endoleaks, of which there are 5 different types, involve blood flow within the aneurysm sac and outside the endograft lumen and can lead to an increased risk of aneurysmal expansion and rupture. A Type I endoleak occurs when blood flows between the stent graft and the blood vessel wall; typically at the proximal (often renal) or distal (often iliac) end of the graft. This complication may also occur as a result of movement of the graft away from the desired location, sometimes called migration. Type II endoleaks occur when blood flows backwards (retrograde) into the aneurysm sac from arteries originating from the aneurysm sac itself (typically the lumbar, testicular or inferior mesenteric arteries). Type III endoleaks occur when blood leaks between the junction sites of "articulated" or "segmented" stent grafts; these multi-component stent grafts are inserted as separate segments which are then assembled inside the artery into their final configuration. Detecting and confirming accurate assembly and fluid-tight contact between the different segments is difficult and current verification methods of correct assembly are suboptimal. Type IV endoleaks occur when cracks or defects develop in the stent graft fabric and blood is able to leak directly through the graft material. Lastly, Type V endoleaks are leakage of blood into the aneurysm sac of an unknown origin. Regardless of their cause, endoleaks are frequently a medical emergency and early detection, characterization and monitoring of them is an important unmet medical need. Incidence rates vary from 15% to 52%, and most patients require either a surgical or endovascular intervention.

The risk of aneurysm rupture is related to aneurysm size, with large aneurysms more likely to rupture than small aneurysms. Due to the risks of early repair, most patients with abdominal aortic aneurysms (AAAs) are only eligible for treatment when their aneurysms have progressed to the point of imminent rupture. There is no solution to prevent disease progression when AAAs are at a relatively harmless stage (smaller than ~5 cm). These patients are under "active surveillance" (annual or semi-annual imaging protocols), tracking their aneurysm's growth until it reaches a large enough threshold for treatment. In the meantime, these patients are living their lives knowing they have up to an 8% risk of rupture.

There are an estimated 13 MM people worldwide currently living with an abdominal aortic aneurysm. When left untreated, all AAAs will eventually rupture if given enough time. A ruptured AAA is associated with up to a 90% mortality rate and is a contributing factor for 2% of all deaths. AAAs are estimated to cause over 200,000 deaths every year worldwide. With a rapidly growing worldwide population of elderly patients with a significantly higher risk of developing aortic aneurysms, there is a need for solutions to improve the standard of care of endovascular aortic aneurysm repair.

In some embodiments, the methods and systems disclosed and described herein are useful to treat aneurysms after a patient has undergone an EVAR procedure and requires additional treatment to alleviate the aneurysm. In some embodiments, the methods and systems disclosed and described herein are useful to treat, repair, and/or prevent endoleaks after, during, and/or before a patient has undergone an EVAR procedure. In some embodiments, the methods and systems disclosed and described herein are useful to treat aneurysms by alleviating blood pressure at a target vascular site. In some embodiments, the methods and systems disclosed and described herein are useful to reduce the severity, frequency, and/or duration of adverse events related to the treatment of aortic aneurysms.

Disclosed herein, in some aspects, is a method of treating an aortic aneurysm in a subject, the method comprising: advancing a shunt through a venous puncture site of a vein to access an arterial puncture site of an artery, the arterial puncture site disposed within the aortic aneurysm or upstream of the aortic aneurysm; and securing the shunt to the artery and vein by deploying i) an arterial sealing structure coupled to a distal end of the shunt, and ii) deploying a venous sealing structure coupled to a proximal end of the shunt, thereby enabling fluid to flow from the artery to the vein.

In some embodiments, advancing the shunt occurs contemporaneous or substantially contemporaneous with an implantation of an endograft within the aortic aneurysm. In some embodiments, advancing the shut occurs after an implantation of an endograft within the aortic aneurysm. In some embodiments, advancing the shunt comprises: inserting a catheter within the vein, the catheter being steerable via a catheter handle coupled thereto; and extending a sliding sheath from the catheter, the sliding sheath detachably coupled to the shunt.

In some embodiments, securing one or both of the arterial sealing structure and the venous sealing structure comprises withdrawing the sliding sheath away from the artery. In some embodiments, one or both of the arterial sealing structure and the venous sealing structure are self-expandable. In some embodiments, the aortic aneurysm is an abdominal aortic aneurysm. In some embodiments, one or both of the arterial and venous sealing structures are pivotally attached to the shunt. In some embodiments, the shunt comprises a shunt body made of a compliant material capable of stretching and shrinking. In some embodiments, the shunt body comprises a lumen therein so as to enable the fluid to flow from the artery to the vein. In some embodiments, prior to securing the shunt, the method includes puncturing the vein to define the venous puncture site, puncturing the artery to define the arterial puncture site, and after puncturing the artery, delivering an endograft to the aortic aneurysm. In some embodiments, the method includes puncturing the artery to define the arterial puncture site and after puncturing the artery, delivering an endograft to the aortic aneurysm.

Disclosed herein, in some aspects, is a method of treating an aortic aneurysm in a subject, the method comprising: implanting a graft within a subject to at least partially bypass a fluid flow through an artery around the aortic aneurysm, the graft having a lumen therein. In some embodiments, the graft is fluidly coupled to the artery at i) a first location upstream of the aortic aneurysm to receive the fluid, and ii) a second location downstream of the aortic aneurysm to deliver the fluid back to the artery. In some embodiments, the graft passes through a portion of a vein. In some embodiments, implanting the graft comprises: inserting a catheter within the artery; passing the artery through the second location of the artery to exit the artery; advancing the catheter to the first location of the artery; passing the catheter through the first location; advancing the graft over the catheter; deploying a first sealing structure to secure and seal the graft at the first location; deploying a second sealing structure to secure and seal the graft at the second location; and withdrawing the catheter. In some embodiments, one or both of the first and second sealing structures are self-expandable. In some embodiments, wherein the aortic aneurysm is an abdominal aortic aneurysm.

Disclosed herein, in some aspects, is an apparatus. The apparatus may include a shunt defining a central portion and having an arterial sealing structure at a first end of the central portion and a venous sealing structure a second, opposite end of the central portion, the arterial sealing structure and the venous sealing structure both being expandable from a delivery configuration to a deployed configuration. In some embodiments, the shunt of the apparatus is configured to be implanted such that at least a portion of the venous sealing structure is positioned in a vein and at least a portion of the arterial sealing structure is positioned in an artery adjacent to the vein to enable blood flow from the artery to the vein via a lumen defined by the shunt.

In some embodiments, the central portion of the shunt narrows in the deployed configuration such that the shunt forms an hourglass shape. In some embodiments, the central portion of the shunt narrows in the deployed configuration such that the shunt forms a dumbbell shape. In some embodiments, when the shunt is in the deployed configuration, the venous sealing structure is configured to form a seal with a wall of the vein and the arterial sealing structure is configured to form a seal with a wall of an artery. In some embodiments, the venous sealing structure includes a first shape corresponding to fluid properties of the vein and the arterial sealing structure includes a second shape different from the first shape and corresponding to fluid properties of the artery. In some embodiments, the apparatus further includes a cover coupled to the central portion to provide structural radial support, the arterial sealing structure and the venous sealing structure being more flexible than the central portion with the cover coupled thereto. In some embodiments, at least a portion of the shunt is formed of bioabsorbable material designed to degrade over time. In some embodiments, the apparatus further includes a flow control device disposed within the central portion and configured to allow blood glow from the arterial sealing structure towards the venous sealing structure and prevent blood flow from the venous sealing structure to the arterial sealing structure. In some embodiments, the apparatus further includes at least one inflatable device coupled to the shunt and configured to control a diameter along a length of the shunt when the shunt is in the deployed configuration. In some embodiments, the first inflatable device is coupled to the venous sealing structure and a second inflatable device is coupled to the arterial sealing structure, the first inflatable device configured to control a diameter of the venous sealing structure and the second inflatable device configured to control a diameter of the arterial sealing structure when the shunt is in the deployed configuration. In some embodiments, the venous sealing structure and the arterial sealing structure are each configured to pivot relative to the central portion to maintain a fluid tight seal with surrounding tissue after the shunt is deployed.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

Figure 1A:
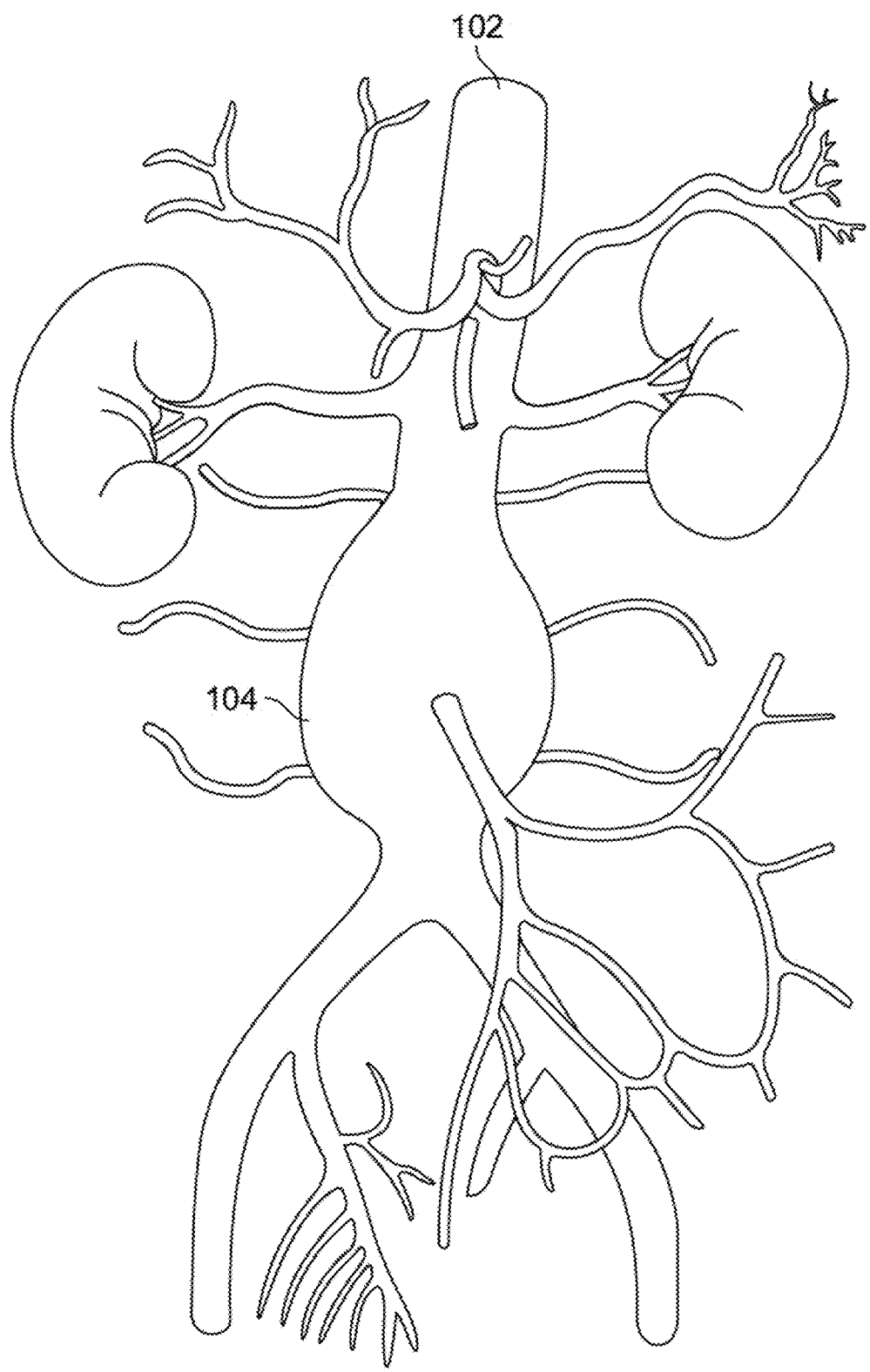
FIG. 1A is a schematic drawing showing an abdominal aortic aneurysm. The drawing shows the aorta, the right kidney, the left kidney, and multiple arterial vessels that branch out from the aorta.

The methods described herein are useful for the treatment of blood vessel weakening and/or bulging conditions (e.g., aneurysms). In some embodiments, the methods herein described are applicable to any condition where a lumen in a body is in need of repair due to the weakening and/or abnormal extension of the lumen wall.

Definitions

Terms used in the claims and specification are defined as set forth below unless otherwise specified.

It must be noted that, as used in the specification, the singular forms "a," "an" and "the" include plural referents unless the context clearly dictates otherwise.

The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e., "one or the other but not both") when preceded by terms of exclusivity, such as "either," "one of," "only one of," or "exactly one of."

The term "about," as used herein, means approximately, in the region of, roughly, or around. Unless otherwise stated for a numerical value noted, when the term "about" is used in conjunction with a numerical range, it modifies that range by extending the boundaries above and below the numerical values set forth. Unless otherwise stated for a numerical value noted, the term "about" is used herein to modify a numerical value above and below the stated value by a variance of 1%, 2%, 3%, 4%, 5%, 6%, 7%, 8%, 9%, 10%, 15%, 20%, 25%, or 50%. For nonlimiting example, a range of "about 2 to about 20" can mean 1.98 to 22, or 1 to 30, or other ranges therebetween. Unless otherwise stated for a percentage range noted, when the term "about" is used in conjunction with a percentage range, it modifies that range by extending the boundaries above and below the percentages set forth. Unless otherwise stated for the percentage noted, the term "about" is used herein to modify a percentage above and below the stated percentage by 1%, 2%, 3%, 4%, 5%, 6%, 7%, 8%, 9%, 10%, 15%, 20%, 25%, or 50% (as an absolute, which may be limited to 0% as a minimum), or by a percentage of the stated percentage i.e. 1% 2%, 3%, 4%, 5%, 6%, 7%, 8%, 9%, 10%, 15%, 20%, 25%, or 50% of the percentage. For nonlimiting example, a range of "about 2% to about 20%" can mean 1% to 21%, or 0% to 70%, or other ranges therebetween, or 1.98% to 22%, or 1% to 30% (as a percentage of the percentage range). For nonlimiting example, a percentage value of "about 30%" can mean 29% to 31%, or 0% to 80%, or other ranges therebetween, or 27% to 33%, or 15% to 45% (as a percentage of the percentage value), or other ranges therebetween. Unless otherwise stated for a numerical range noted, numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about."

The term "subject," as used herein, is meant to include both human and non-human animals. Exemplary human subjects include human patients (referred to as patients) with a disorder (e.g., an aortic aneurysm) or normal subjects. The term "non-human animal" in one aspect of the invention includes all vertebrates, such as non-mammals (e.g., chickens, amphibians, reptiles), and mammals, such as non-human primates, domestic and/or agriculturally useful animals, such as sheep, dogs, cats, cattle, pigs, and the like.

The term "substantially," as used herein, is a broad term, and is to be given its ordinary and customary meaning to a person of ordinary skill in the art (and is not to be limited to a special or customized meaning), and refers without limitation to being largely but not necessarily wholly that which is specified. For example, the term "to substantially separate," as used herein refers to the removal, whether completely or partially (e.g., removal of 1% or more, 5% or more, 10% or more, 20% or more, 30% or more, 40% or more, 50% or more, 60% or more, 70% or more, 80% or more, 90% or more, 95% or more, 96% or more, 97% or more, 98% or more, 99% or more, or 99.9%), of an unwanted constituent from a mixture containing two or more constituents mixed together.

The terms "treat," "treating," or "treatment of" (or grammatically equivalent terms), as used herein, refer to reducing, at least partially improving, or ameliorating the severity of a subject's condition. For example, the methods and systems herein described are useful for treating aortic aneurysms in order to prevent disease evolution and alleviate at least one clinical symptom of the aortic aneurysm for example, alleviating pressure to the blood vessel wall within or near the aneurysm and/or reduction in aneurysm size and or volume.

Systems for Treating Aortic Aneurysms

Figure 1B:
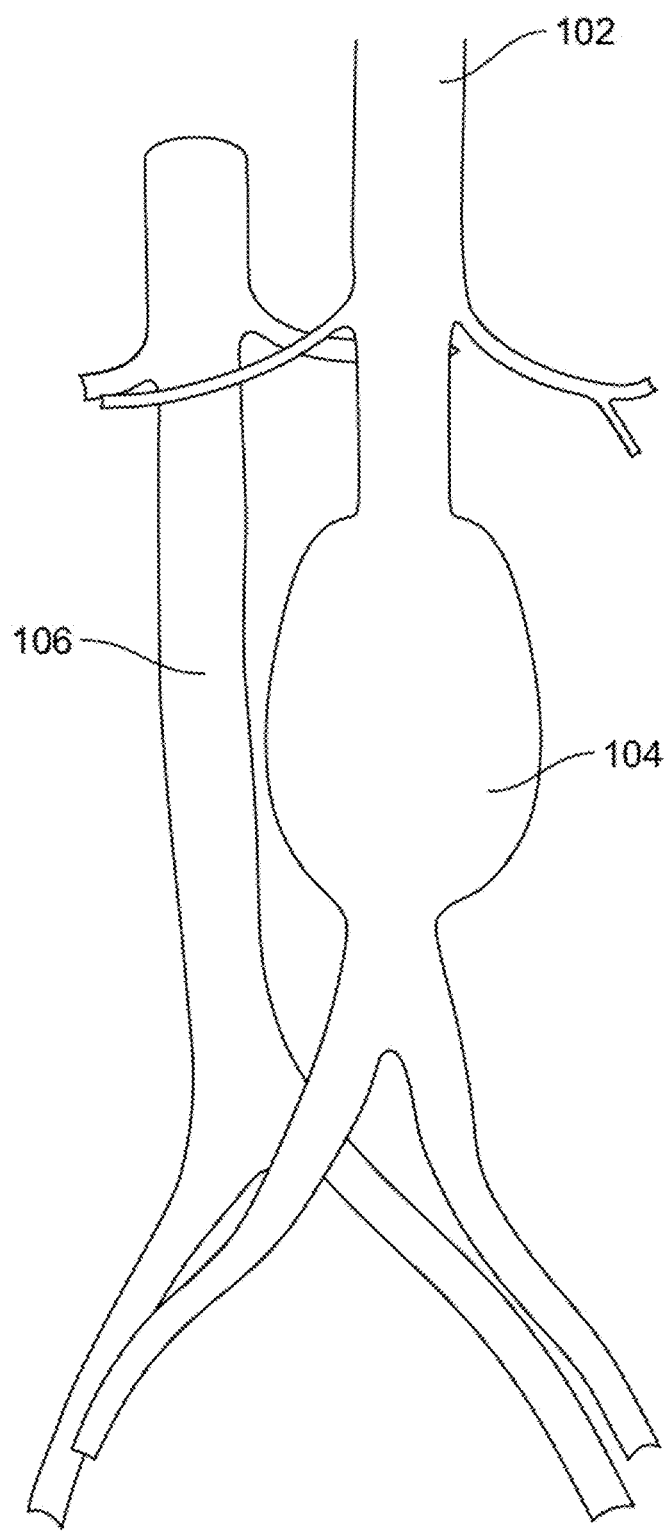
FIG. 1B is another schematic showing an aortic aneurysm.

Described herein, in some aspects, are systems and methods for treating aortic aneurysms (FIGS. 1A-1B provides an exemplary depiction of an aortic aneurysm depicting an aorta 102, vena cava 106, and the site of the aneurysm (e.g., aneurysm sac 104)). In some embodiments, treating aortic aneurysms helps prevent an aneurysm rupture, reduce an aneurysm size (e.g., aneurysm sac size), alleviates hypertension within the aneurysm, or any combination thereof.

There have been several case studies showing the presence of an aortocaval fistula providing immediate benefit to patients after EVAR by shunting blood from the aneurysm sac to the inferior vena cava, resulting in rapid shrinkage of AAAs despite persistent endoleaks. Accordingly, a device configured for creating a fluid connection between the inferior vena cava and the sac of an abdominal aortic aneurysm would provide a safe and effective alternate means of improving post-procedural outcomes following endovascular aortic aneurysm repair. Transcaval access provides an improved access route for endovascular aortic interventions in aortic interventions, particularly for patients unsuitable for traditional access routes including femoral, subclavian, transapical, and aortic. This approach involves percutaneous advancement of a guidewire into the abdominal aorta via initial access from the femoral vein through the adjoining inferior vena cava.

In some embodiments, treating aortic aneurysms comprises relieving pressure build-up and/or reducing blood flow through the impacted region experiencing the aneurysm. In some embodiments, a shunt (e.g., transcaval shunt) is implanted from an adjacent vein (e.g., vena cava) and passed through an aortic wall so as to allow blood to flow from the artery (e.g., abdominal aorta) to the vein (e.g., vena cava). In some embodiments, said shunt is used to help alleviate, reduce, eliminate, and/or prevent fluid build-up resulting from one or more endoleaks. In alternate or additional embodiments, a bypass graft is implanted so as to bypass all or some of the blood flow around the aneurysm (e.g., aneurysm sac). In some embodiments, systems and methods described herein are used to treat an aortic aneurysm after a subject has undergone an Endovascular Aortic Aneurysm Repair (EVAR) procedure to implant a stent-graft prosthesis (herein referred to as an endograft).

Shunt Implantation

As described herein, in some embodiments, a shunt is implanted within a subject from a vein (e.g., vena cava 106) to an artery (e.g., aorta 102), so as to alleviate pressure build-up of blood flow within an aortic aneurysm, prevent progression of an aortic aneurysm, and/or drain or remove fluid within the aneurysm sac (e.g., build-up fluid resulting from an endoleak).

Figure 2:
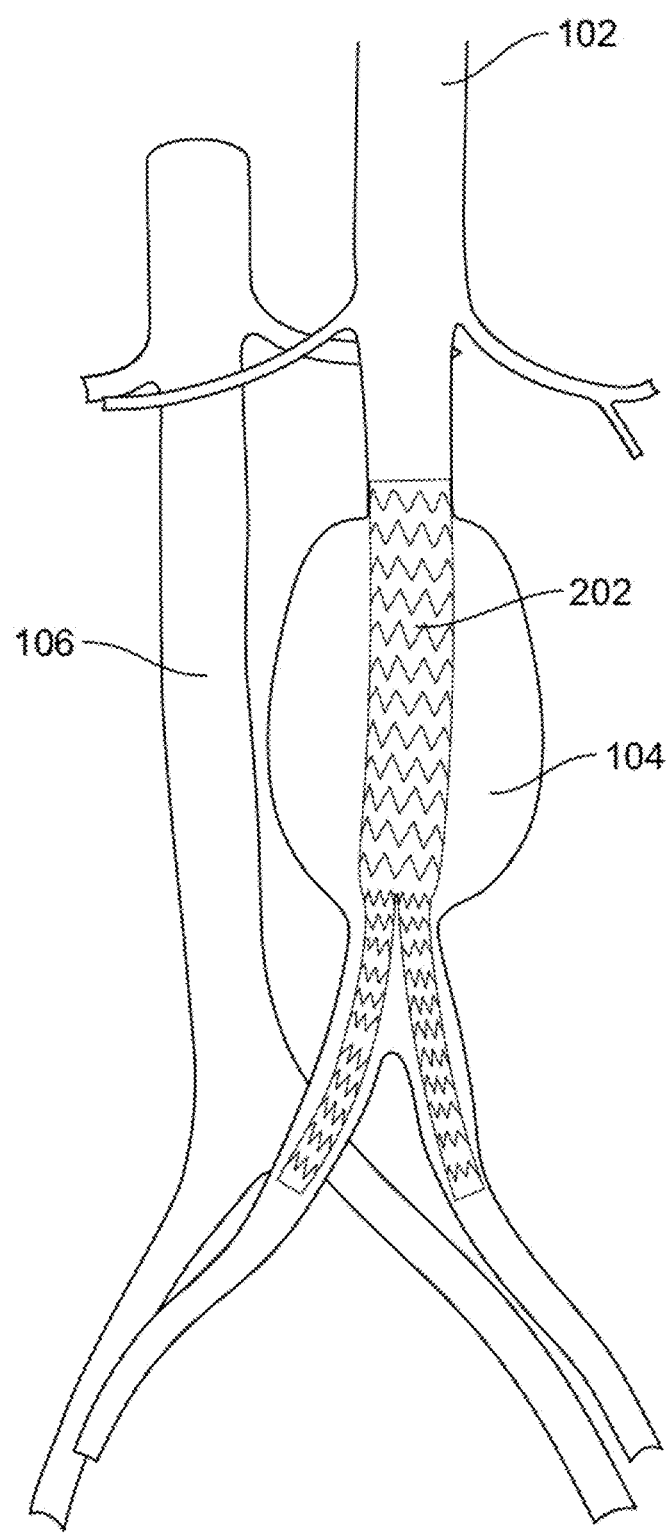
FIG. 2 is a schematic of the aortic aneurysm of FIG. 1B depicting an endograft implanted therein to avoid fluid (e.g., blood flow) impacting the vessel wall at aneurysm sac.
Figure 3:
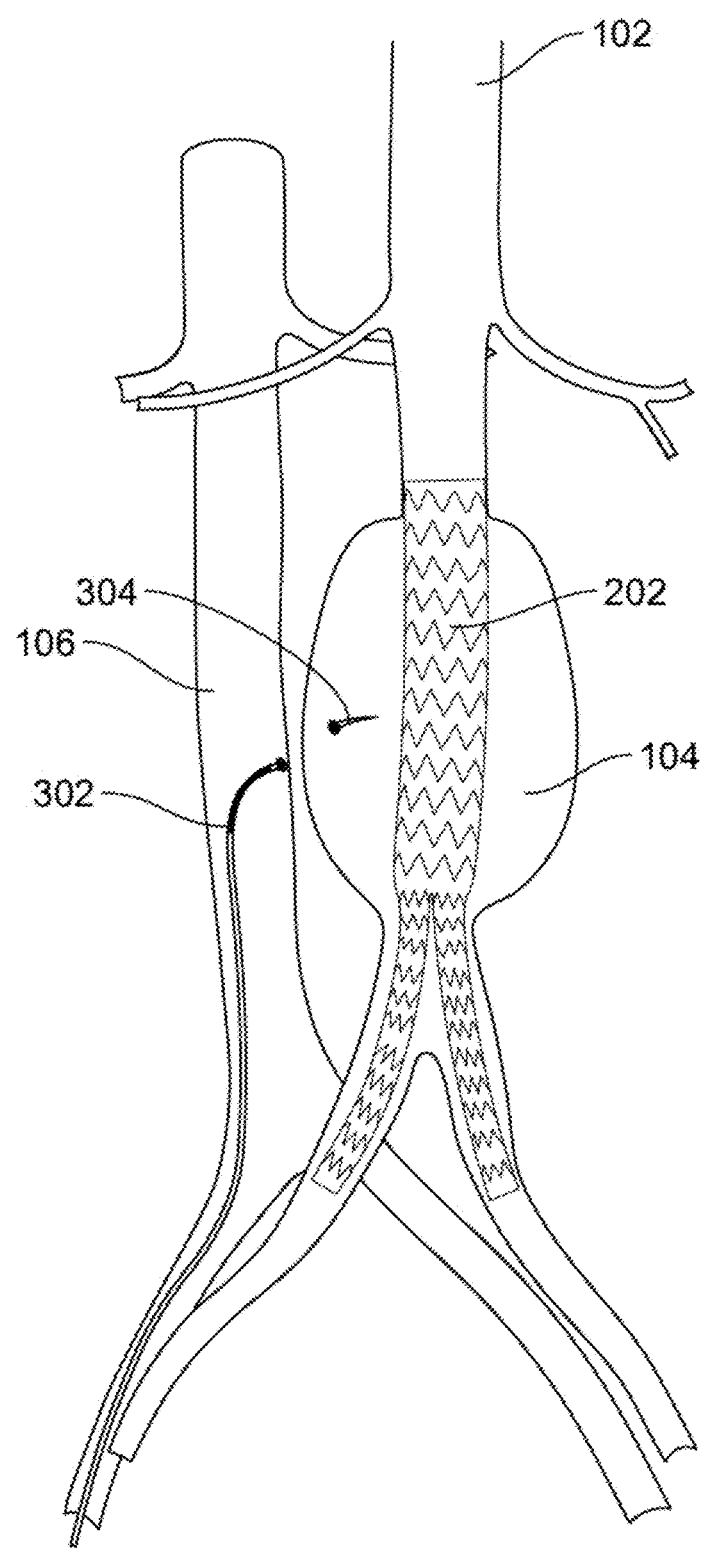
FIG. 3 is a schematic drawing showing transcaval penetration of an access catheter from the vena cava to the aortic aneurysm towards the endograft shown in FIG. 2, according an embodiment herein.
Figure 4:
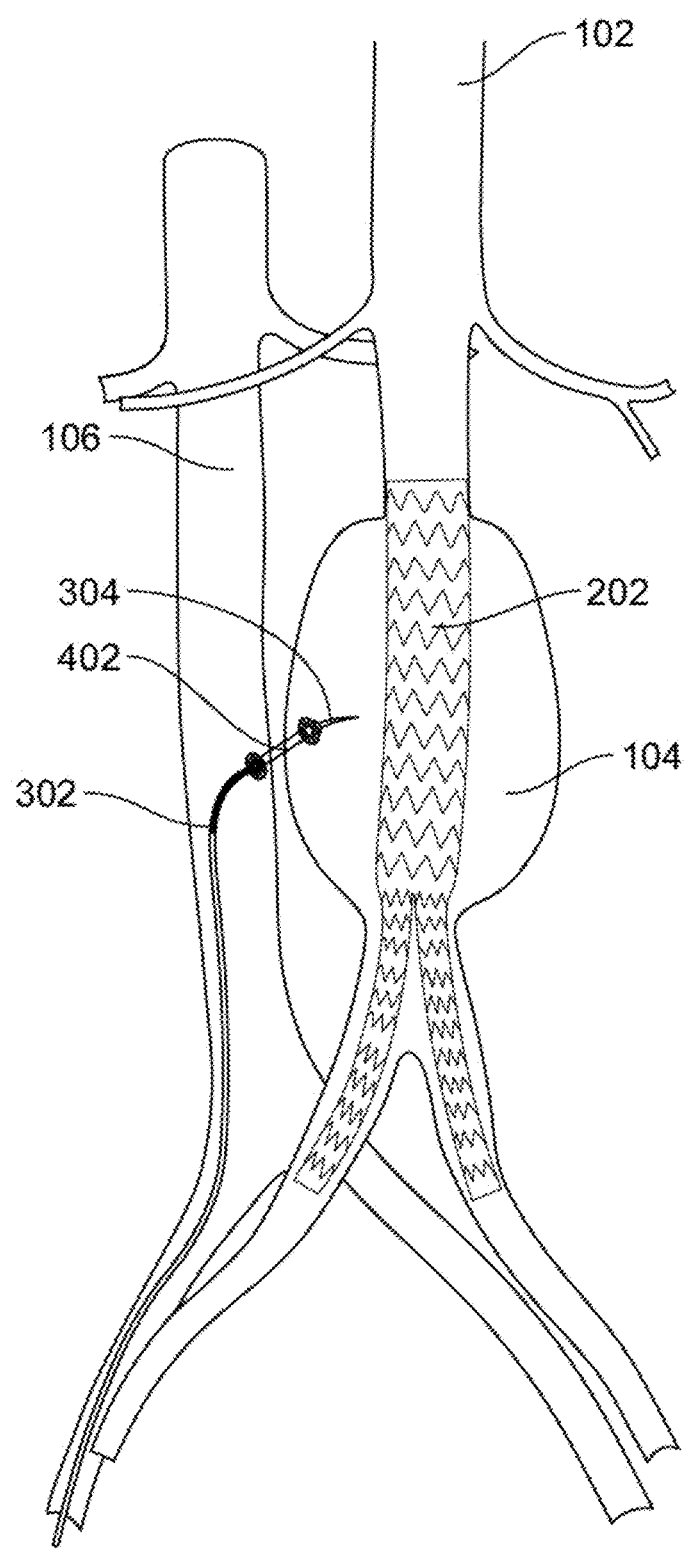
FIG. 4 is a schematic drawing showing a shunt connecting the vena cava and the aorta of the aneurysm shown in FIG. 2, according an embodiment herein.
Figure 5A:
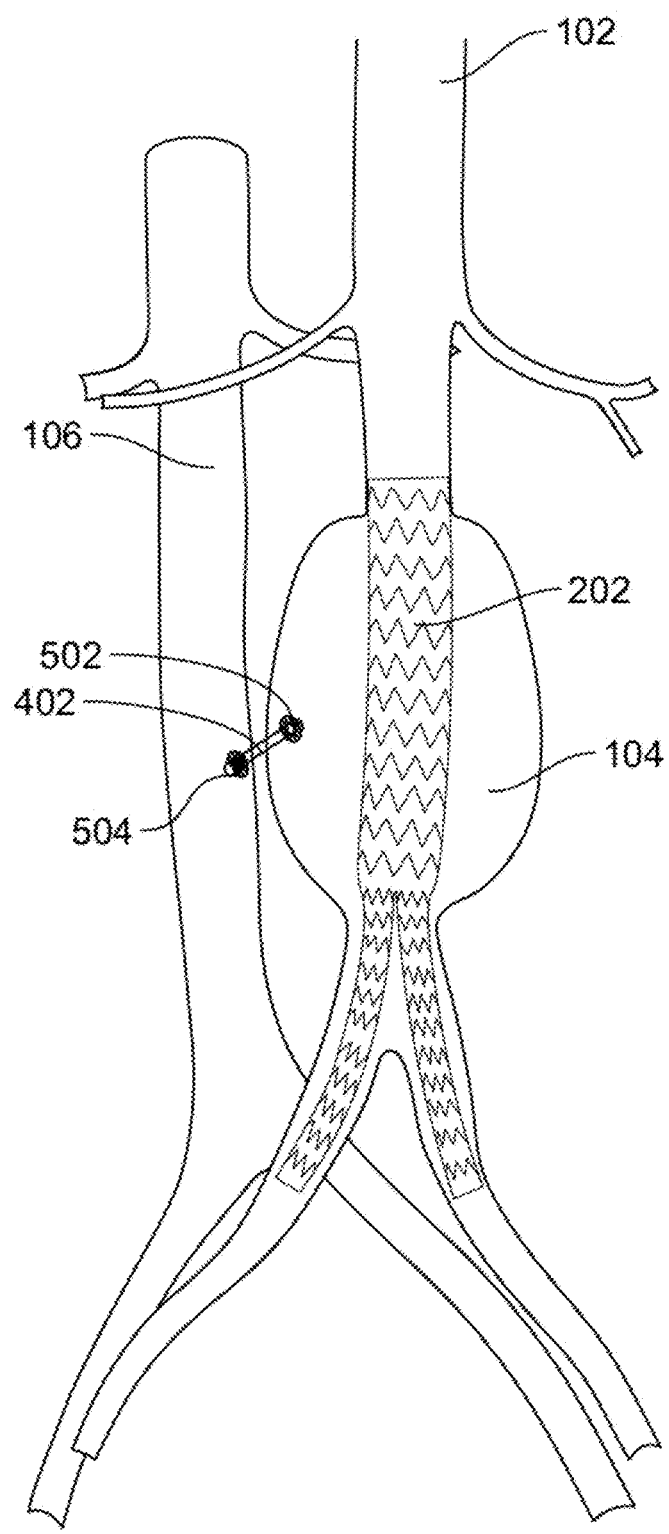
FIGS. 5A-5B are schematics showing a shunt including a distal sealing structure and a proximal sealing structure of the aneurysm shown in FIG. 2, according an embodiment herein, wherein blood flows from the aorta to the vena cava, and wherein there is extravascular space therebetween.
Figure 5B:
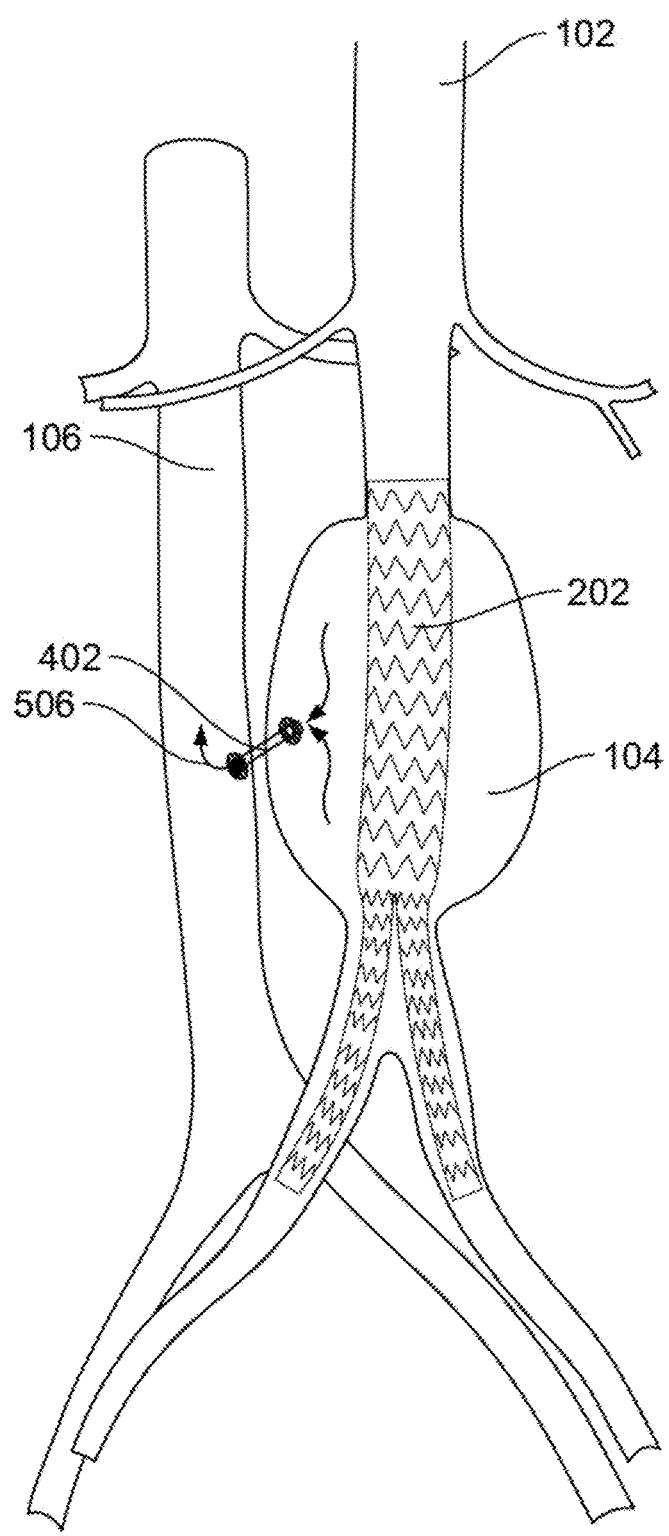
Figure 6A:
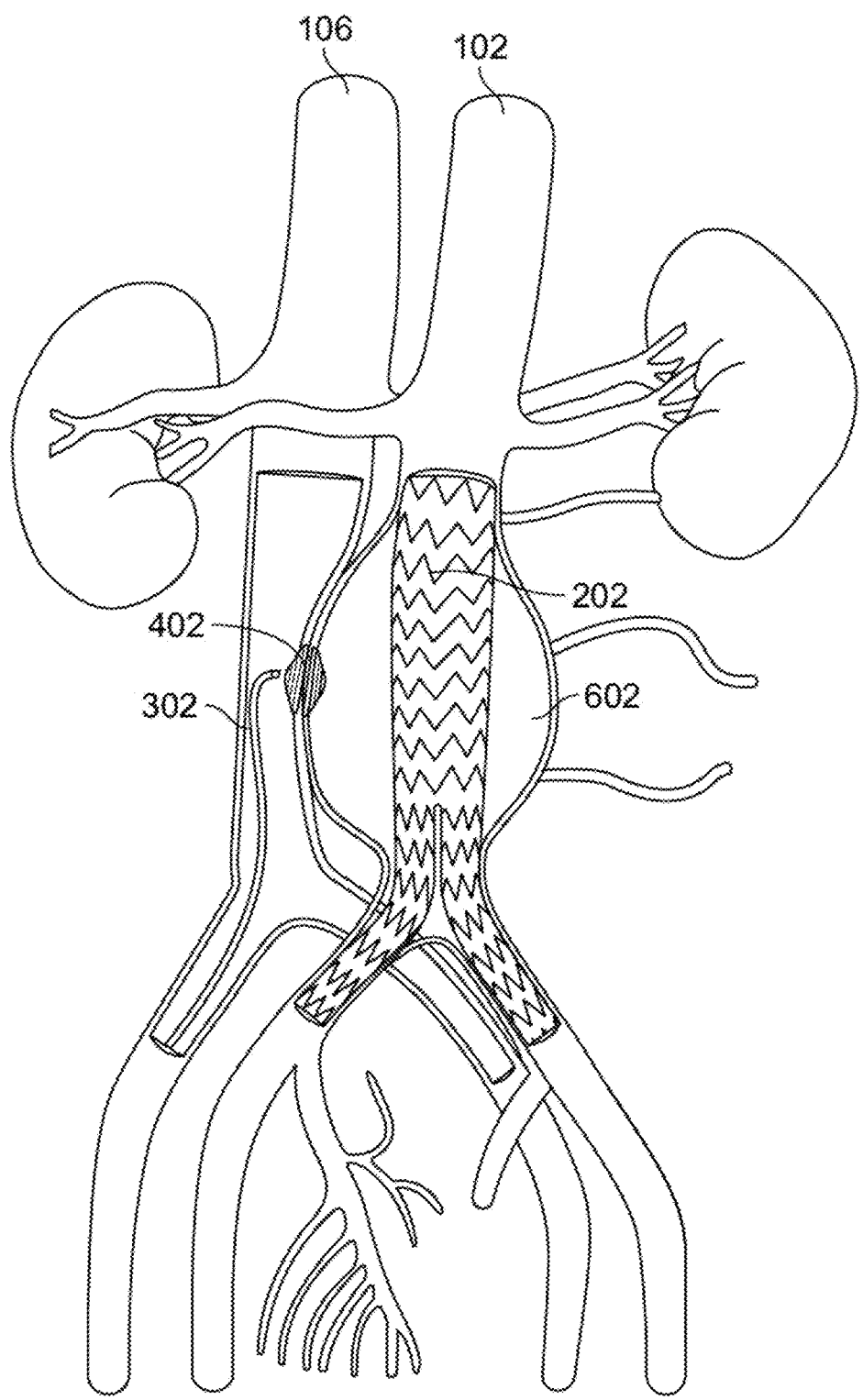
FIGS. 6A-6B are schematics showing a shunt implanted between the vena cava and an abdominal aortic aneurysm of the aneurysm shown in FIG. 2 and blood flowing therebetween, according an embodiment herein, wherein the vessel wall of the aneurysm abuts the vessel wall of the vena cava.
Figure 6B:
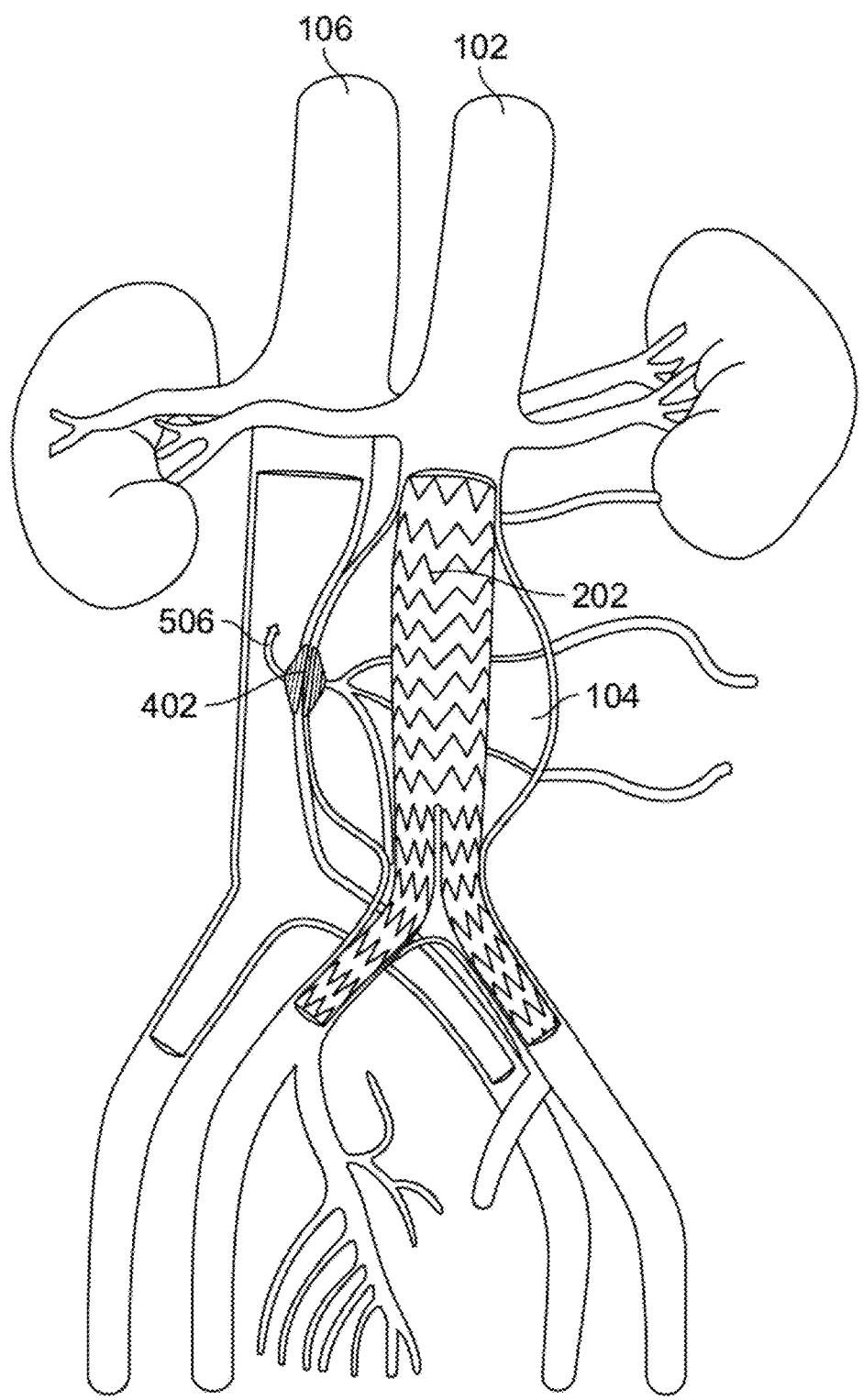

In some embodiments, a method for treating, repairing, and/or preventing endoleaks after, during, and/or before a patient has undergone an EVAR procedure comprise creating a fluid connection between the sac of an aortic aneurysm to another region of lower pressure (such as the vena cava). This lower pressure passage effectively decreases the arterial resistance and allows for pressures within the aneurysm sac to be reduced by offloading some of the volume of blood leaking into aneurysm sac to other areas. As depicted, FIG. 2 shows an endograft 202 placed as an initial treatment for an aortic aneurysm (e.g., abdominal aortic aneurysm), wherein the fluid (e.g., blood) flows entirely through the endograft, thereby alleviating pressure build-up and stress against the aortic wall at the aneurysm. In some cases, however, one or more leaks may form about the endograft, such that fluid (e.g., blood) builds up at the aneurysm site (e.g., aneurysm sac 104), and potentially resulting in further stress and/or rupture of the aortic wall. For example, type 2 endoleaks are the most common type of endoleak and are described as a refilling of the aortic sac via branches such as lumbar arteries (LAs), inferior mesenteric artery (IMA), median sacral artery, or accessory renal arteries. Accordingly, in some cases, providing a shunt between the artery (e.g., aorta 102) and vein (e.g., vena cava 106) will help to drain fluid (e.g., blood) being collected within the aneurysm sac to alleviate further progression of the aneurysm and potential rupture. FIGS. 3-4 provide an exemplary method for implanting the shunt (described further herein), and FIGS. 5A-6B depicts fluid drainage from the aortic aneurysm sac to the vena cava. At a high level, FIG. 3 depicts a catheter 302 inserted into the vena cava 106, and piercing through a venous puncture site and an arterial puncture site so as to access the aneurysm sac (FIG. 3), thereafter wherein a shunt 402 is implanted (FIG. 4). FIGS. 5A and 5B depict the catheter removed and blood flowing out 506. In some case, FIG. 5B depicts an extravascular space between the vena cava 106 and aorta 102. FIGS. 6A and 6B depict a shunt 402 and blood flowing out 506, wherein the aorta 102 wall at the aneurysm site 104 abuts the wall of the vena cava 106.

Figure 7:
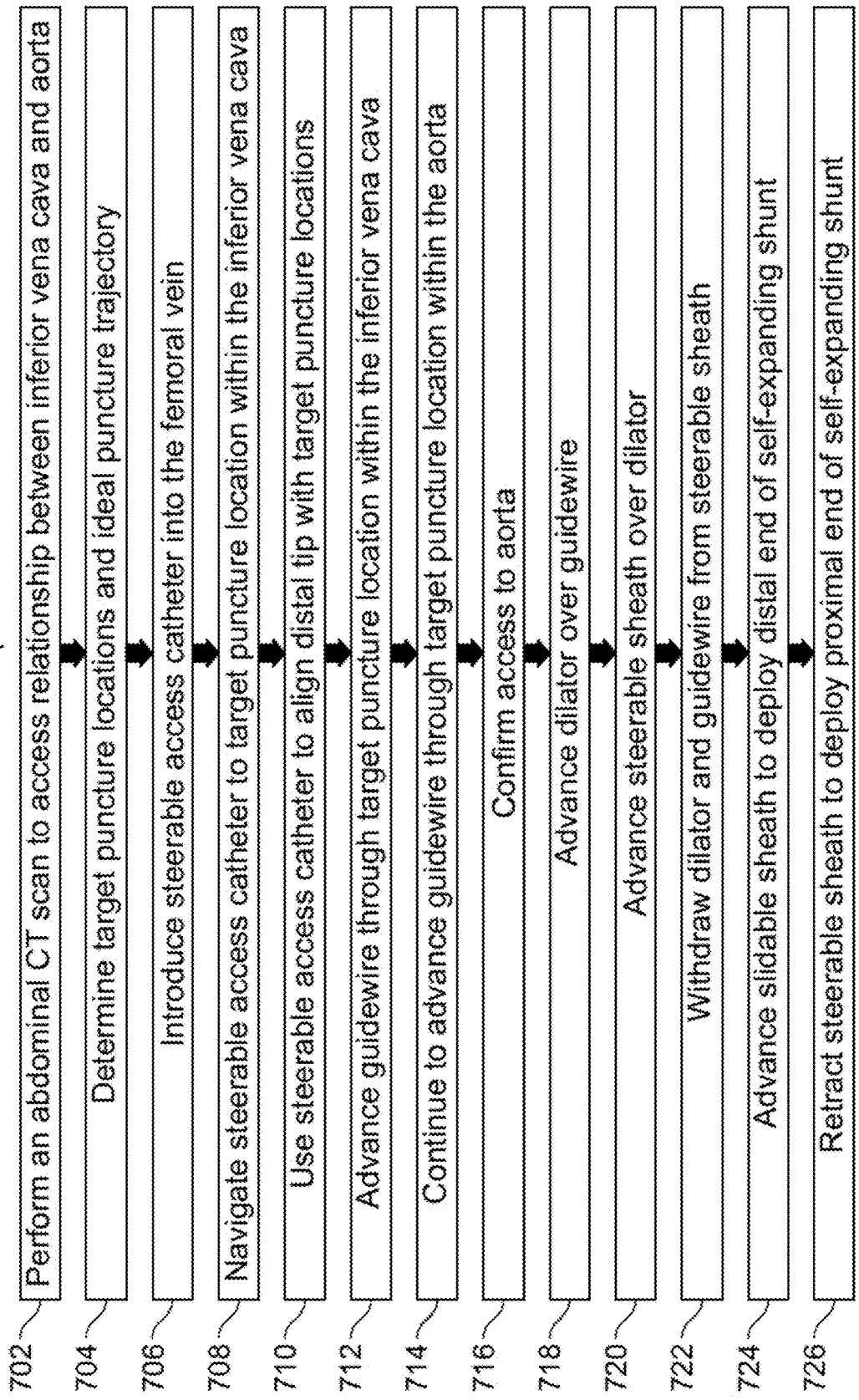
FIG. 7 is a flow diagram showing an exemplary process for implanting a shunt between a vena cava and aorta, according an embodiment herein.

FIG. 7 provides an exemplary method for implanting a shunt e.g., as depicted in FIGS. 3-6B). With respect to FIGS. 8-21, the method of implanting a shunt for treatment of an aorta aneurysm is described herein. In some embodiments, said method for implanting a shunt occurs contemporaneous or substantially contemporaneous with when an endograft is implanted to treat an aneurysm, as a preventive care means in the event a leak occurs across the endograft. In some embodiments, said method for implanting a shunt occurs after the endograft has been implanted, as a preventive care means or as a remedial response to the leakage of fluid into the sac of an aortic aneurysm.

FIGS. 8-11B depict an overview of system 800 components for implanting the transcaval shunt 402 (as described further herein). In some embodiments, the system 800 comprises a catheter 302, a guidewire 902, a dilator 904, a sliding sheath 912, and the shunt 402. FIG. 9A depicts the components of the catheter assembly individually, while FIG. 9B depicts the catheter assembly assembled.

In some embodiments, the catheter includes a catheter handle 926 and a catheter shaft 924, extending therefrom, and having a catheter lumen therein. In some embodiments, the catheter 302 is steerable (e.g., a steerable sheath), as depicted with the multiple positions of a distal portion of the catheter shaft. In some embodiments, the catheter handle 926 comprises a hemostatic valve 916 at a proximal end of the catheter handle 926. In some embodiments, the catheter handle 926 comprises a rotation collar 920 for steering the catheter shaft 924. In some embodiments, the catheter handle 926 comprises a tip rotation indicator 918 to determine a rotation of a dilator tip 808 (as described herein). In some embodiments, the catheter 302 comprises a contrast port 922 coupled to the catheter handle 926.

In some embodiments, the catheter 302 includes one or more (e.g., 1, 2, 3, 4, 5, 6, 7, 8, 9, or 10) catheter radiopaque markers 802. In some embodiments, one or more radiopaque markers are disposed at the distal end of the catheter shaft 924. In some embodiments, the one or more catheter radiopaque markers 802 comprises a radiopaque band.

In some embodiments, the catheter shaft 924 has a length of from about 10 cm to about 100 cm. In some embodiments, the catheter shaft 924 has a catheter wall forming a catheter inner diameter and a catheter outer diameter. In some embodiments, the catheter inner diameter is from about 0.5 cm to about 2 cm. In some embodiments, the catheter outer diameter is from about 0.5 cm to about 2 cm.

As described herein, in some embodiments, the proximal end of the catheter shaft 924 is operably connected to the catheter handle 926. In some embodiments, the position of the catheter shaft 924 inside the blood vessel (e.g., artery or vein) is controlled by a person (e.g., a surgeon, a medical specialist, a doctor, or similar) or by a machine (e.g., a robotic arm). In some embodiments, the position of the catheter shaft 924 inside the blood vessel is controlled using the catheter handle 926. In some embodiments, the catheter handle 926 includes a release mechanism operably linked to any one or more of the guidewire 902, dilator 904, the sealing structures (502, 504), the shunt 402, the sliding sheath 912, or the catheter shaft 924. In some embodiments, the catheter handle is configured to orient the direction of any one or more of the guidewire 902, the sliding sheath 912, the shunt 402, or the dilator 904.

In some embodiments, a guidewire 902 is configured to pass through a dilator 904. In some embodiments, the guidewire 902 includes a proximal end and a distal end. The guidewire 902 may additionally include a guidewire lumen traversing the length of the guidewire 902 from the proximal end to the distal end. In some embodiments, the guidewire 902 has a length of from about 10 cm to about 250 cm. In some embodiments, the guidewire has a guidewire wall forming a guidewire inner diameter and a guidewire outer diameter. In some embodiments, the guidewire inner diameter is from about 0.1 mm to about 3 mm. In some embodiments, the guidewire outer diameter is from about 0.1 mm to about 3 mm.

In some embodiments, the guidewire 902 is introduced within the dilator 904 via a guidewire introduction port 908. In some embodiments, the dilator comprises one or more depth markings 906, configured to indicate how far the dilator 904 has extended from a point of reference (e.g., a distal end of the catheter handle 926). In some embodiments, the dilator 904 body serves as a support member 304 (as described herein). In some embodiments, the dilator 904 comprises a dilator tip 808, configured to be rotated, and configured to dilate the opening at a venous and/or arterial puncture site (as described herein). In some embodiments, the dilator tip 808 is configured to be rotated via the catheter handle 926.

In some embodiments, the dilator includes one or more (e.g., 1, 2, 3, 4, 5, 6, 7, 8, 9, or 10) dilator radiopaque markers 806. In some embodiments, the dilator radiopaque markers are disposed at the distal end of the support member 304 (dilator body), proximal to the dilator tip 808. In some embodiments, the dilator 904 has a length of from about 10 cm to about 100 cm. In some embodiments, the dilator 904 has a wall forming a dilator inner diameter and a dilator outer diameter. In some embodiments, the dilator inner diameter is from about 0.1 mm to about 5 mm. In some embodiments, the dilator outer diameter is from about 1 mm to about 5 mm.

In some embodiments, a sliding sheath 912 is configured to slide over the dilator 904. In some embodiments, the sliding sheath 912 is configured to be detachably coupled to the shunt 402 at a distal portion of the sliding sheath 912. In some embodiments, the sliding sheath 912 comprises a braided shaft 914. In some embodiments, the sliding sheath 912 is configured to maintain the sealing structures 502, 504 in a non-deployed state until the sliding sheath 912 is withdrawn (as described herein).

Figure 10:
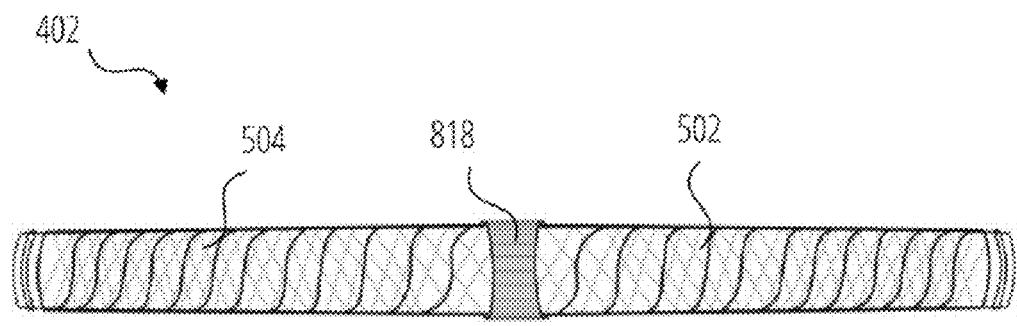
FIG. 10 is a schematic of the treatment method of FIG. 8, showing the shunt in a deployed configuration, according an embodiment herein.
Figure 11A:
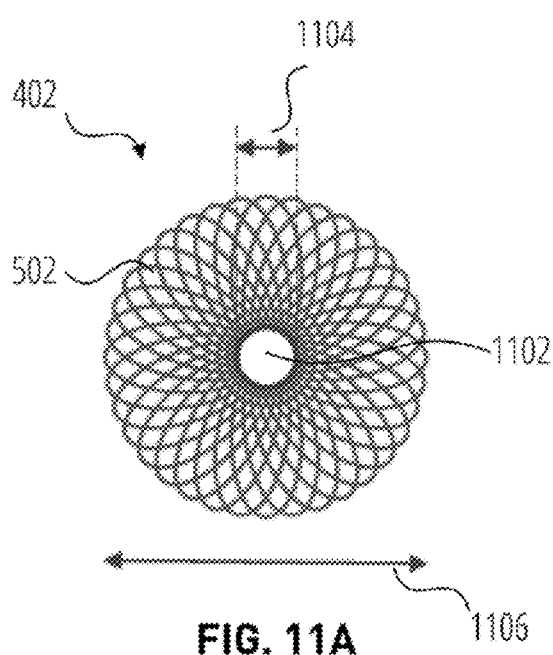
FIGS. 11A-11B are schematics of the treatment method of FIG. 8, a distal, front view (FIG. 11A) and a side view (FIG. 11B) of the shunt with the sealing structures in a deployed configuration, according an embodiment herein.
Figure 11B:
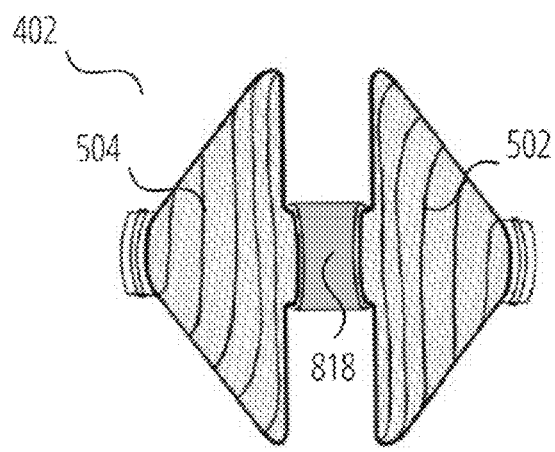
Figure 12:
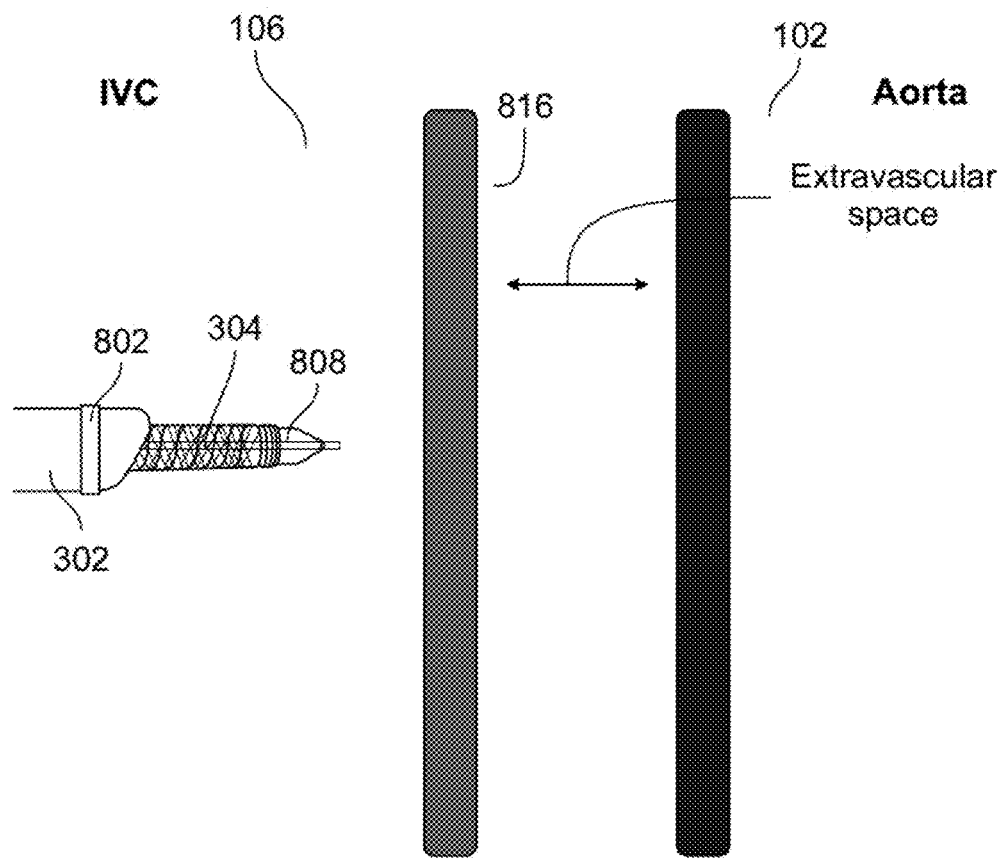
FIG. 12 is a schematic of the treatment method of FIG. 8, showing a steerable access catheter positioned and pointed towards a target puncture location for transcaval access to the aorta, according an embodiment herein.
Figure 13:
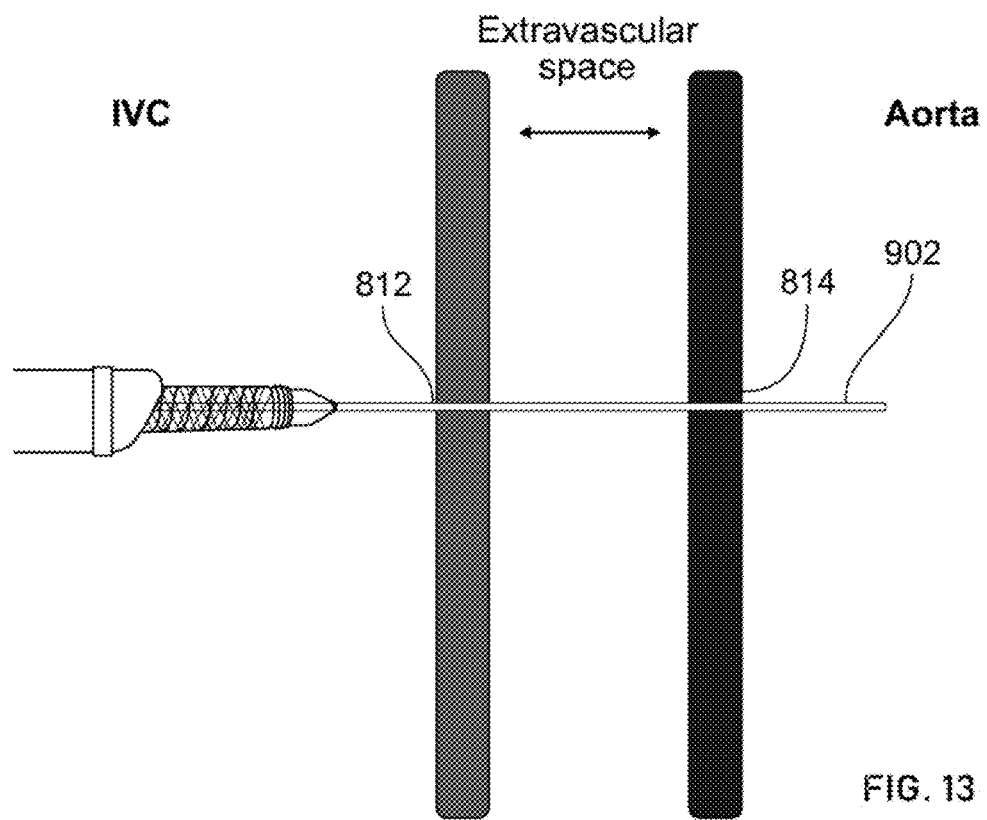
FIG. 13 is a schematic of the treatment method of FIG. 12, showing the deployment of the guidewire establishing transcaval access from the vena cava to the aorta, according an embodiment herein.

With reference to FIG. 10, a shunt 402 in a non-deployed configuration is depicted. In some embodiments, the shunt 402 comprises a distal sealing structure 502 (arterial sealing structure), a proximal sealing structure 504 (venous sealing structure), and a shunt body 818 having a shunt lumen 1102 (not shown) therethrough. FIG. 11A depicts a deployed, front view of the shunt 402, wherein the distal sealing structure 502 has been deployed. FIG. 11B depicts a side view of a shunt 402 with the distal sealing structure 502 and proximal sealing structure 504 deployed. As described herein, the distal sealing structure 502 and proximal sealing structure 504 help seal the openings at the arterial puncture site 814 and the venous puncture site 812 respectively. In some embodiments, the shaft shunt lumen 1102 has a shunt lumen diameter 1104 diameter from about 0.5 mm to about 100 mm, about 1 mm to about 50 mm, about 2 mm to about 25 mm, about 3 mm to about 15 mm, about 4 mm to about 10 mm, or about 3 mm to about 8 mm. In some embodiments, the shunt lumen 1102 has an diameter of about 0.5 mm to about 100 mm, about 1 mm to about 50 mm, about 2 mm to about 25 mm, about 3 mm to about 15 mm, about 4 mm to about 10 mm, or about 3 mm to about 8 mm. In some embodiments, the deployed distal sealing structure diameter 1106 and/or deployed proximal sealing structure diameter from about from about 0.5 mm to about 200 mm, about 1 mm to about 100 mm, about 5 mm to about 75 mm, about 8 mm to about 50 mm, about 10 mm to about 30 mm, or about 10 mm to about 20 mm.

In some embodiments, the shunt body 818 and corresponding shunt lumen 1102 have a length of from about 10 mm to about 10 cm.

Figure 8:
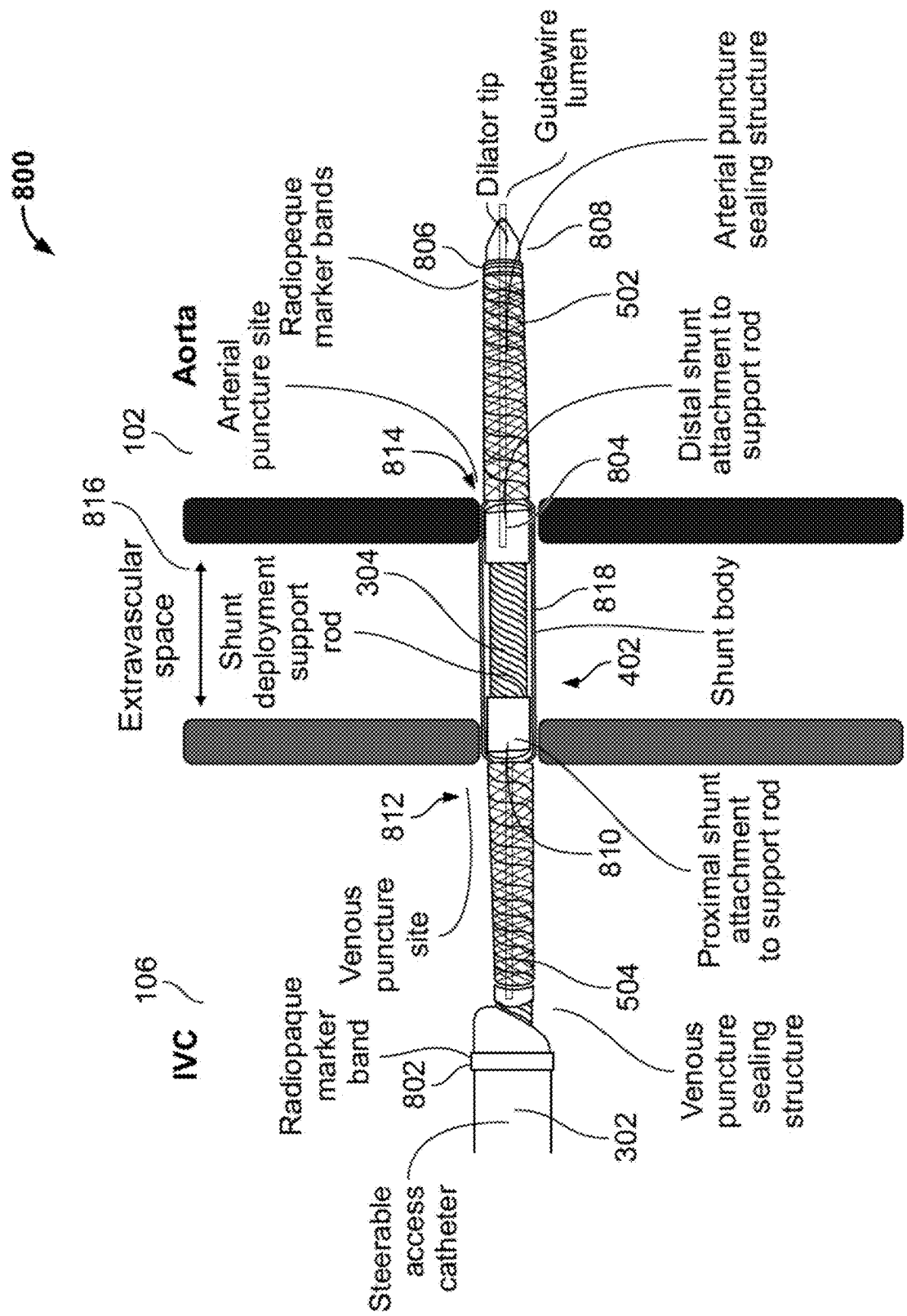
FIG. 8 is a schematic drawing showing a treatment method for an aortic aneurysm, depicting transcaval penetration from the inferior vena cava (IVC) to the aorta for the implantation of a shunt, according an embodiment herein.
Figure 9A:
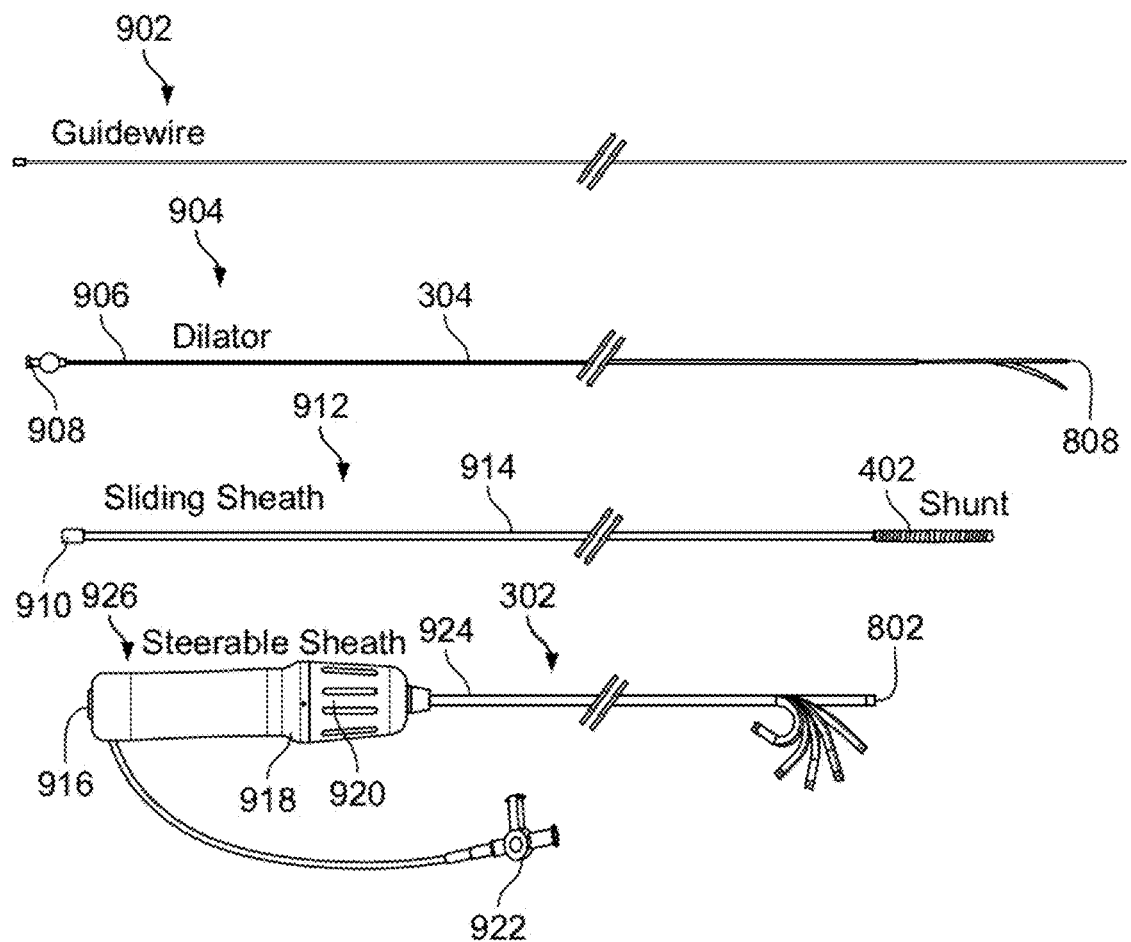
FIGS. 9A-9B are schematics of the treatment method of FIG. 8, showing the components of a system for implanting the shunt, according an embodiment herein.
Figure 9B:
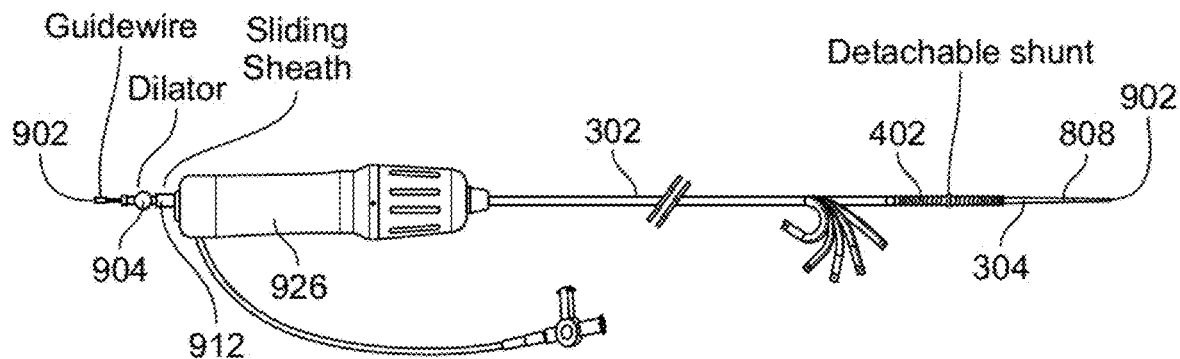

As described herein, in some embodiments, the shunt 402 and the dilator 904 are detachably attached. In some embodiments, the shaft shunt body 818 is attached to the distal sealing structure 502 and proximal sealing structure 504 via a distal sealing structure attachment 804 and proximal sealing structure attachment 810 (FIG. 8). In some embodiments, the shunt includes one or more (e.g., 1, 2, 3, 4, 5, 6, 7, 8, 9, or 10) radiopaque markers. In some embodiments, the radiopaque markers are disposed at the proximal end of the shunt. In some embodiments, the radiopaque markers are disposed at the distal end of the shunt. In some embodiments, the radiopaque markers are disposed at both the proximal and distal ends of the shunt. In some embodiments, one or both of the distal sealing structure 502 and proximal sealing structure 504 are compressed via the sliding sheath 912, and are configured to flare out in a deployed configuration once the slide sliding sheath 912 is withdrawn (as described herein). In some embodiments, one or both of the dist al sealing structure 502 and proximal sealing structure 504 are self-expandable.

In another embodiment, the shunt 402 and the sliding sheath 912 are detachably attached, the shunt 402 being initially held in an undeployed configuration and the sliding sheath 912 being disposed within the inner diameter of the shunt 402. The sliding sheath 912 may include an inflatable balloon disposed its distal end and a proximal balloon inflation port that can be used to expand the shunt from an undeployed configuration to a deployed configuration and/or controllably decouple the shunt from the sliding sheath.

The shunt 402 is preferably positioned so that about half of its length is positioned in the aneurysm sac and the vena cava. As seen in FIGS. 10 and 11A and 11B, the shunt 402 is expanded from an undeployed configuration to a deployed configuration. In one embodiment, the shunt 402 can expand from a relatively uniform cylindrical shape (FIG. 10) to a shape with a narrowed middle section (e.g., an hourglass or dumbbell shape), as seen in FIG. 11B. As the shunt 402 is deployed and expanded, its length substantially decreases. The shunt lumen diameter may increase or decrease during deployment. In one embodiment, the shunt may comprise a laser cut super elastic metal (nitinol) or can be braided from super elastic wires to have a heat set shape.

One variation on the delivery technique of the shunt 402 allows for the shunt lumen to be resized after delivery, if needed. Specifically, the shunt 402 can be delivered as previously described, but the shunt lumen is expanded to an initial diameter that is smaller than the shunt lumen is capable of expanding to. This may be achieved, for example, by further expanding the shunt lumen diameter by inflatable balloon that inflates to a desired diameter.

Alternately, if it is desirable to reduce the diameter of the shunt lumen, a separate delivery catheter may be used to deliver a tubular spacer having a thickness that reduces the size of the shunt lumen. In one example, the tubular spacer may be a secondary shunt structure subsequently deployed inside of the first shunt. The ability to resize the shunt 402 after delivery allows for customization of the amount of shunted fluid for each individual subject. It also allows the shunt 402 to be modified at a later date if the subject's hemodynamic needs change.

In an alternate embodiment, the sliding sheath 902 may include two or three separate, independently inflatable balloons that can be inflated to different sizes to achieve a similar hourglass shape. This may allow for expansion of the shunt lumen to a desired diameter while ensuring the ends of the shunt 402 radially expand sufficiently to engage the surrounding tissue.

A shunt covering may span along at least a portion of the length of the shunt. The shunt covering may aid in anchoring the shunt to the vascular puncture sites and/or prevent the leakage of fluids around the shunt.

The shunt may further incorporate a flow control device that allows flow through the shunt lumen in only one direction or allows flow through the shunt lumen in only one direction and only if certain parameters are met. Alternatively, the shunt may further incorporate a flow control device that allows flow through the lumen in both directions, but only when certain parameters are met. The parameters that must be met in a first direction for fluid flow to be established may be the same or different than the parameters that must be met for fluid to flow in a second direction. Such parameters may include, but are not limited to pressure, pressure gradient, absolute flow or flow gradients.

Thresholds may be built into such a shunt which function to begin or cease shunt at specific local conditions. These are 'onset' or 'offset' thresholds. In each case, for example, pressure or flow acts to change the effective shunt lumen size (open, close, other). The purpose of adaptive shunting is to protect organs or biologic tissues from pressure or flow damage. This protection may be conferred by limiting pressures at either the source or receiving end of the connection. For example, a "bleed off" shunt could be used to drop pressures which are approaching or exceeding a specified threshold value.

With reference to the method in FIG. 7, in implanting a transcaval shunt, in some embodiments, a scan 702 (e.g., CT scan, such as an abdominal CT scan) is performed so as to access a relationship between the vena cava (e.g., inferior vena cava) and the aorta. Accordingly, in some cases, based on the scan performed, the target puncture sites (e.g., arterial puncture site 814, venous puncture site 812) may be identified 704. As used herein, the term "puncture site" may be used interchangeably with the term "puncture location".

With reference to FIG. 7, in some embodiments, the methods of treating an aortic aneurysm include introducing 706 a catheter 302 into a vein (e.g., femoral vein, vena cava 106) of the subject (see e.g., FIG. 12), and navigating 708 the catheter 302 to the venous puncture site 812. In some embodiments, the distal end of the catheter is guided to the venous puncture site using a medical imaging technique. In some embodiments, using the catheter handle, the distal end of the catheter is aligned 710 with the venous puncture site 812. In some embodiments, the catheter radiopaque marker 802 disposed at the distal end of the catheter shaft 924 provide a signal useful to determining the location of the distal end of the catheter shaft 924 in relation with venous puncture site 812 and the arterial puncture site 814. In some embodiments, once the distal end of the catheter shaft 924 is positioned proximate the venous puncture site 812, the guidewire 902 is then advanced through the catheter shaft 924, and extends from the catheter to pierce 712 through the venous puncture site 812 (e.g., see FIG. 13). In some embodiments, the guidewire is continued to be advanced to the aorta to puncture 714 through the arterial puncture site 814 and access the aneurysm sac 104. In some embodiments, access by the guidewire 902 to the aneurysm sac 104 is then confirmed 716 using fluoroscopy.

Figure 14:
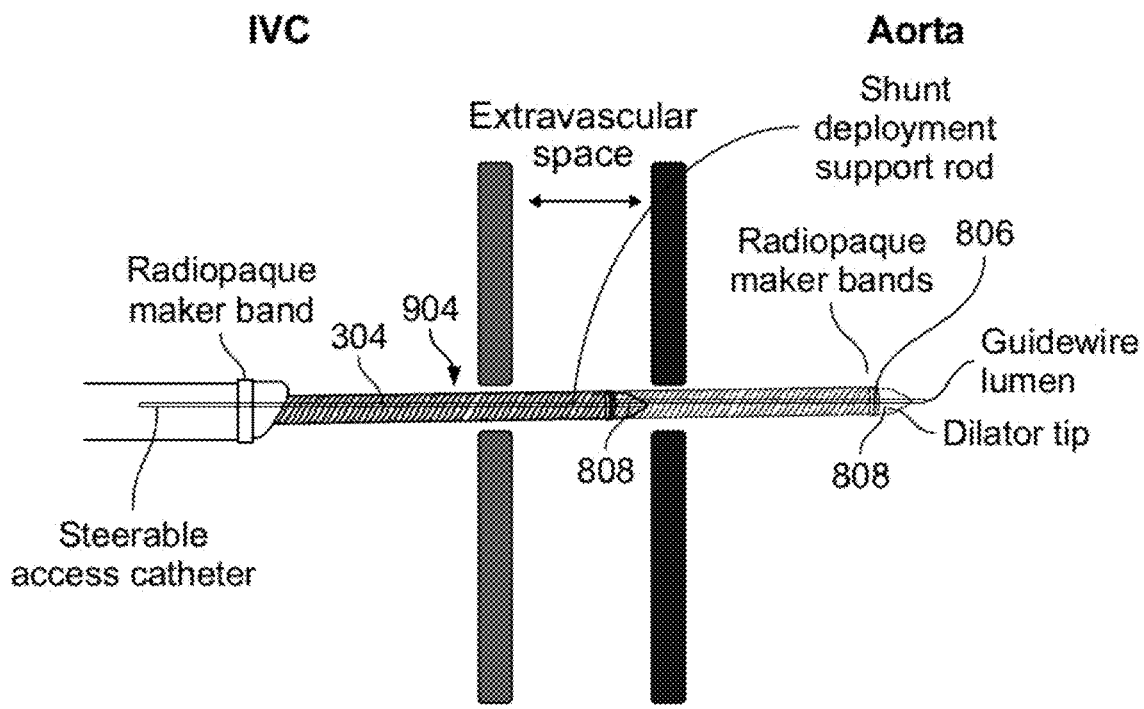
FIG. 14 is a schematic of the treatment method of FIG. 13, showing transcaval penetration of a dilator from the inferior vena cava (IVC) to the aorta, according an embodiment herein.
Figure 15:
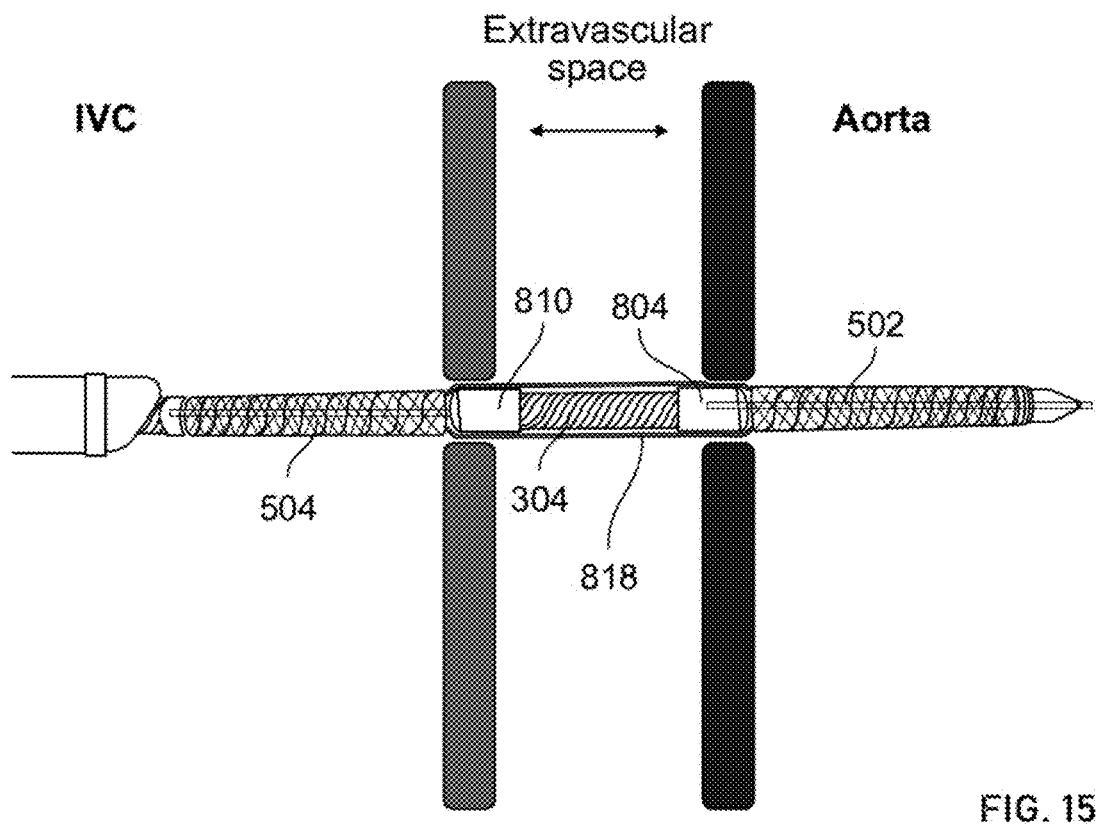
FIG. 15 is a schematic of the treatment method of FIG. 14, showing the deployable sealing structure advanced through the arterial puncture site, and the shunt from FIG. 8 disposed between the vascular puncture sites, according to an embodiment herein.
Figure 16:
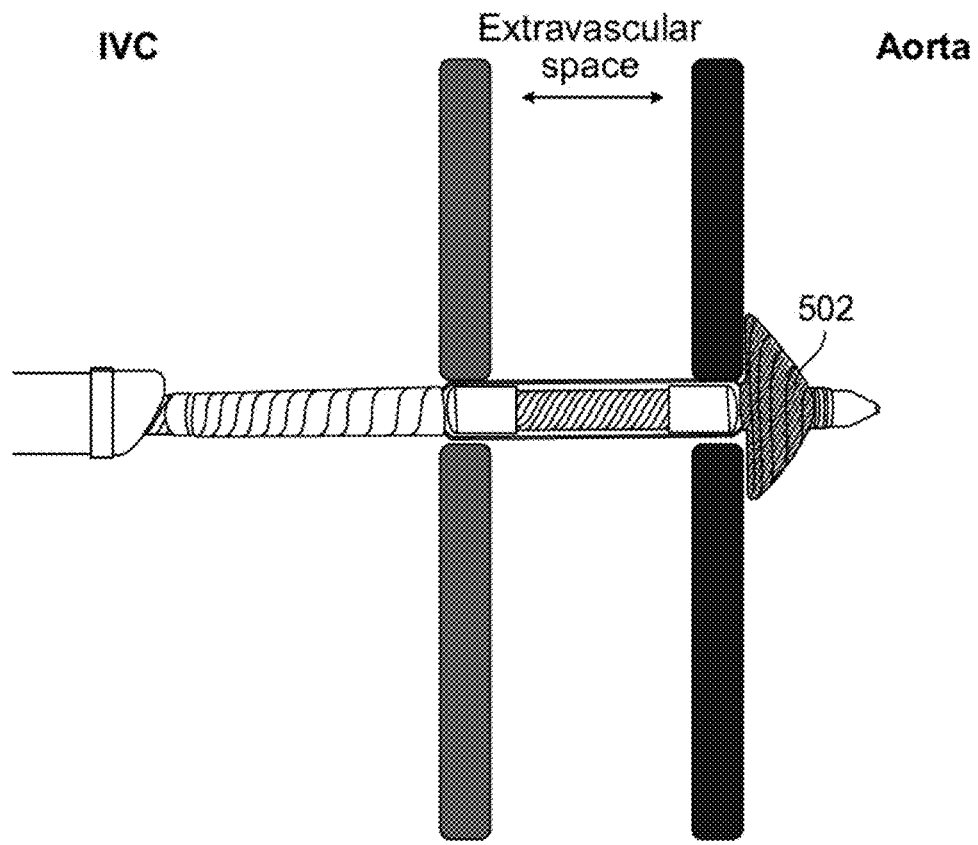
FIG. 16 is a schematic of the treatment method of FIG. 15, showing the deployment of the distal vascular sealing structure, according an embodiment herein.
Figure 17:
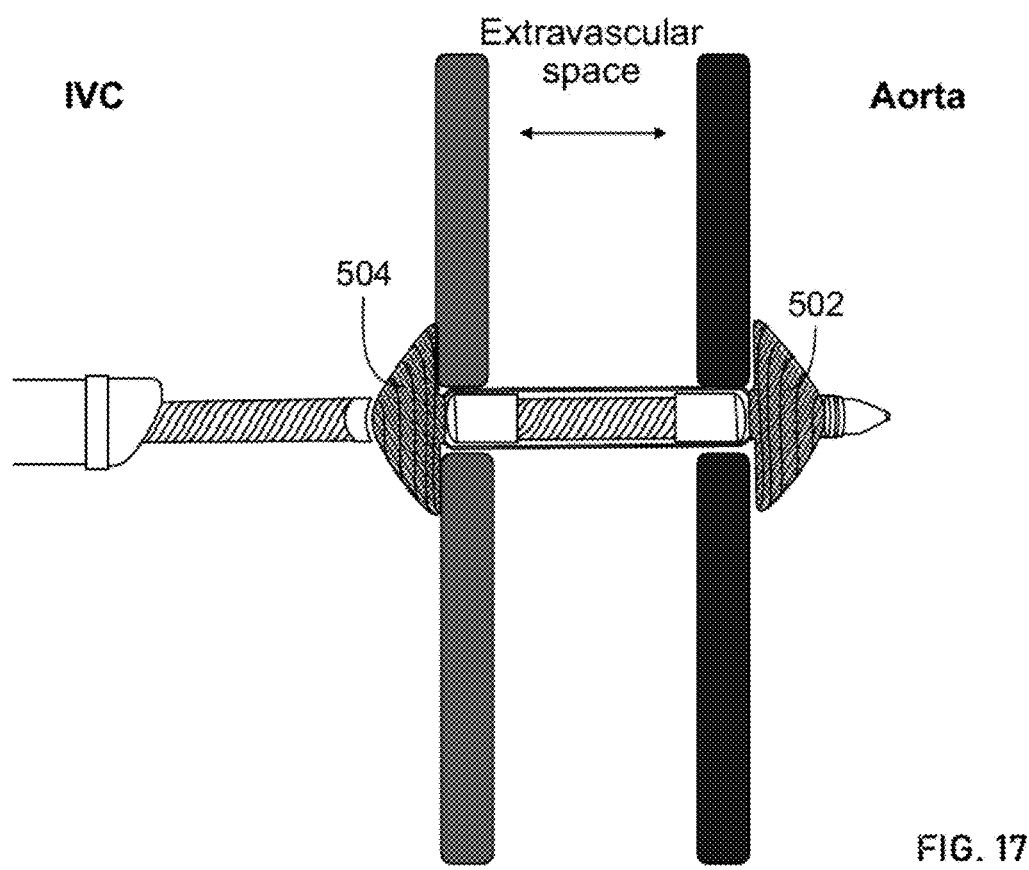
FIG. 17 is a schematic of the treatment method of FIG. 16, showing the deployment of the proximal vascular sealing structure, according an embodiment herein.
Figure 18:
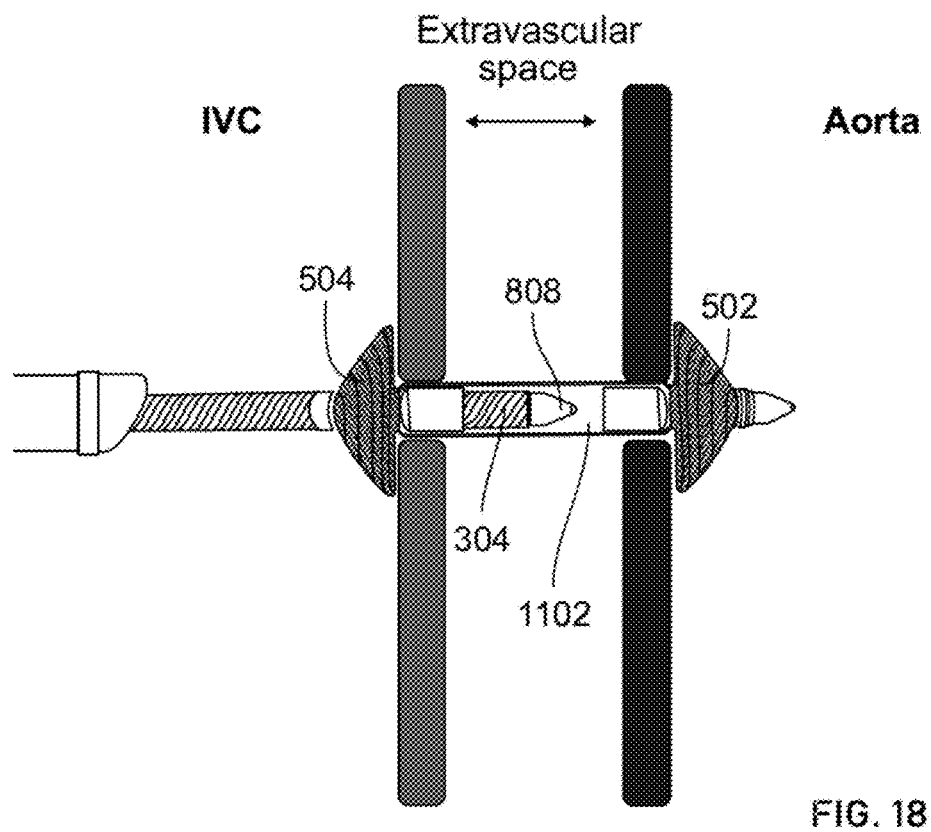
FIG. 18 is a schematic of the treatment method of FIG. 17, showing the shunt being decoupled from the dilator, according an embodiment herein.
Figure 19:
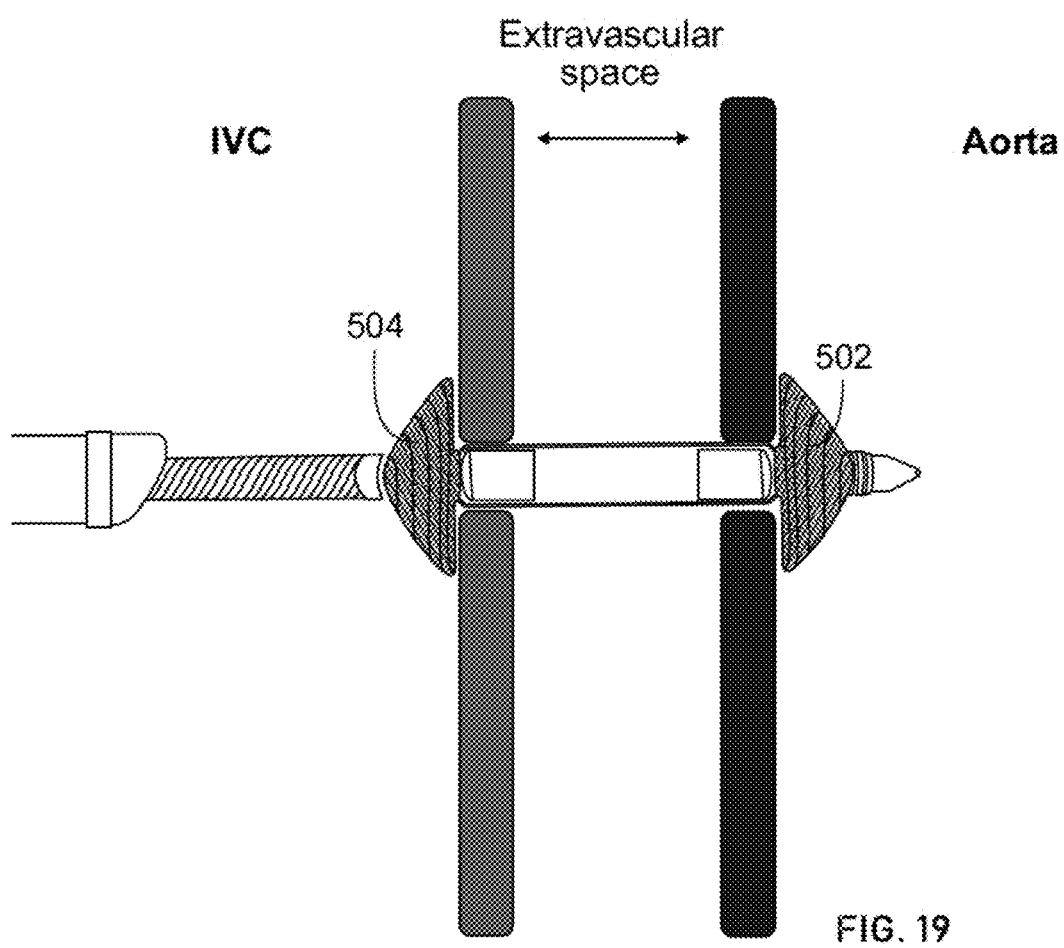
FIG. 19 is a schematic of the treatment method of FIG. 18, showing the dilator withdrawn from the inner lumen of the shunt, according an embodiment herein.
Figure 20:
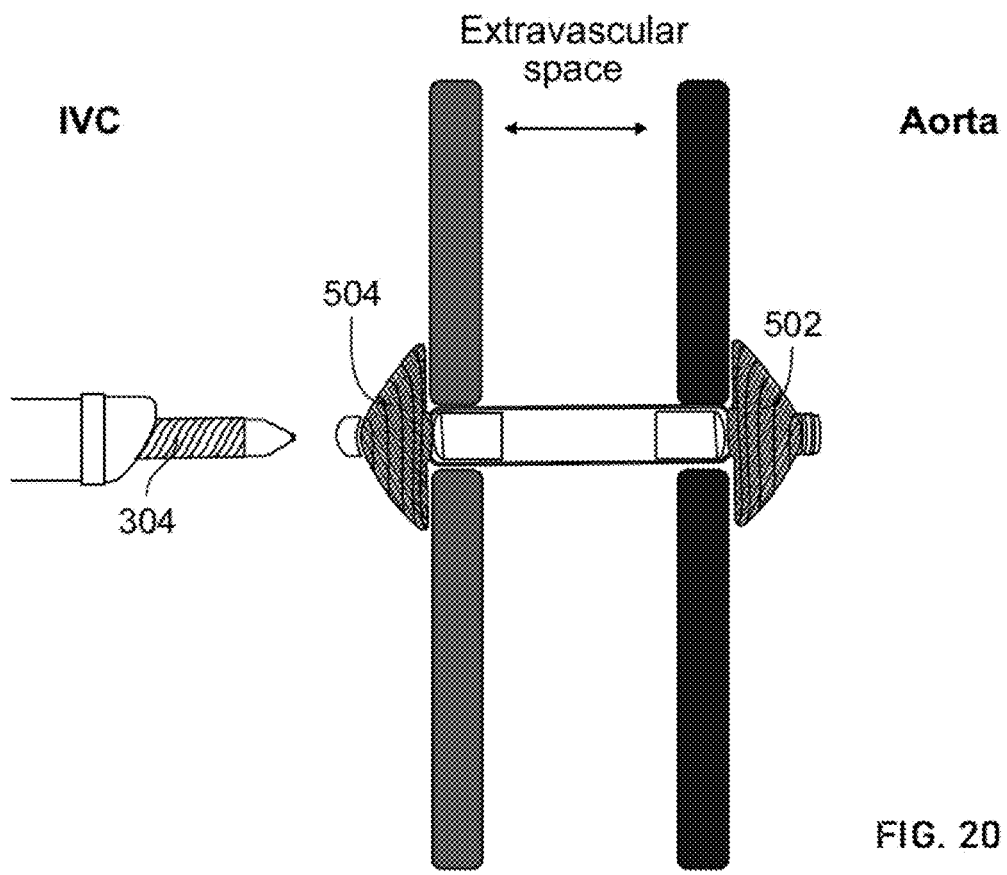
FIG. 20 is a schematic of the treatment method of FIG. 19, showing the dilator fully withdrawn from the inner lumen of the shunt, according an embodiment herein.

In some embodiments, with reference to FIG. 14, the dilator 904 is then advanced 718 over the guidewire 902 and used to increase the opening size at the venous puncture site 812 and the arterial puncture site 814. In some embodiments, the dilator tip 808 is rotated via the catheter handle 926. Accordingly, in some embodiments, the dilator 904 is advanced into the aneurysm sac 104. In some embodiments, a sliding sheath 912 and shunt 402 is advanced 720 over the dilator 904, such that the shunt body 818 and corresponding shunt lumen 1102 therein extend at least partially from the venous puncture site 812 to the arterial puncture site 814. In some embodiments, the dilator 904 body acting acts as a support member 304 for the shunt 402. In some embodiments, the sliding sheath 912 is advanced until at least the distal sealing structure 502 is located within the aorta (e.g., aneurysm sac 104).

In some embodiments, the guidewire 902 and dilator 904 are then withdrawn 722. In some embodiments, the sliding sheath 912 is then withdrawn 724 from the aorta 102, thereby deploying the distal sealing structure 502 (see FIG. 16). In some embodiments, the sliding sheath 912 is then withdrawn to deploy the proximal sealing structure 504, thereby sealing the shunt lumen 1102 between the vena cava 106 and aorta 102. In some embodiments, the catheter 302 is then withdrawn. In some embodiments, the dilator 904 remains within the shunt lumen 1102 to act as a support member 304, particularly when there exists at least some extravascular space 816 between the vena cava 106 and aorta 102. In some embodiments, the support member 304 is withdrawn after the sliding sheath 912 is withdrawn.

Figure 21:
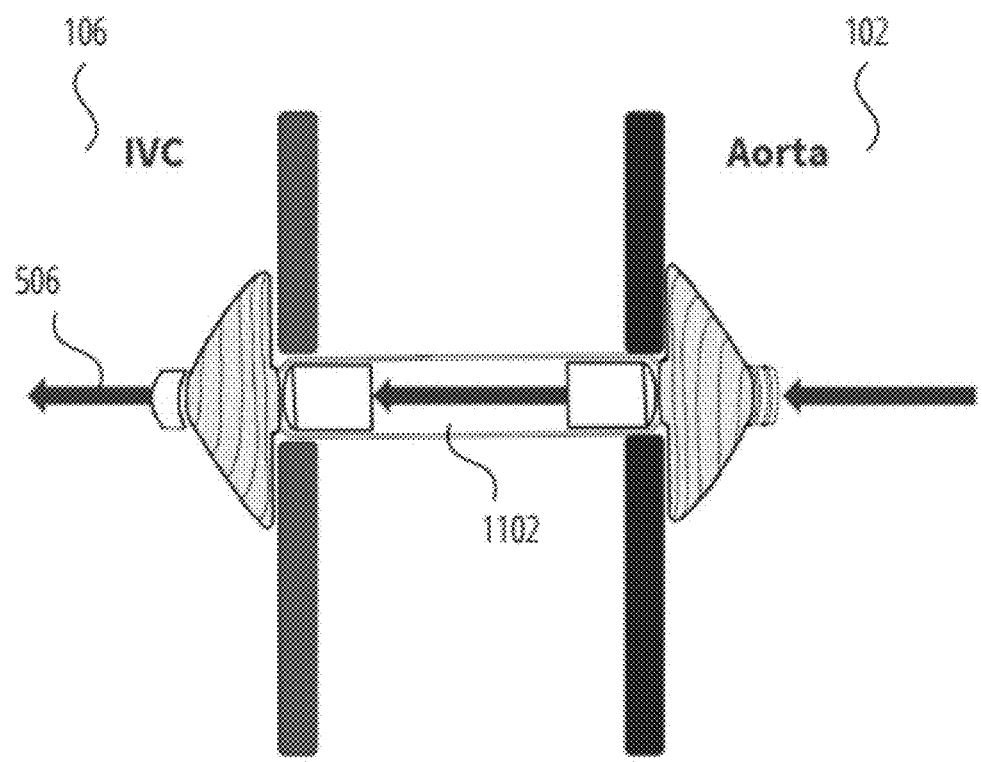
FIG. 21 is a schematic of the treatment method of FIG. 20, showing the shunt permitting fluid flow from the aorta to the vena cava, according an embodiment herein.

In some embodiments, the implanted shunt serves to continuously drain fluid (e.g., blood) from the aneurysmal sac into the vena cava (FIG. 21). Accordingly, in some embodiments, the shunt, via the deployed distal sealing structure 502 and proximal sealing structure 504 help form a circumferential fluid seal around the vascular puncture sites permitting fluid flow from the aorta to the vena cava.

In some embodiments, the systems herein disclosed and described include one or more (e.g., 1, 2, 3, 4, 5, 6, 7, 8, 9, or 10) steerable access catheters, one or more (e.g., 1, 2, 3, 4, 5, 6, 7, 8, 9, or 10) guidewires, one or more (e.g., 1, 2, 3, 4, 5, 6, 7, 8, 9, or 10) dilators, one or more sliding sheaths, and one or more (e.g., 1, 2, 3, 4, 5, 6, 7, 8, 9, or 10) shunts.

Figure 22:
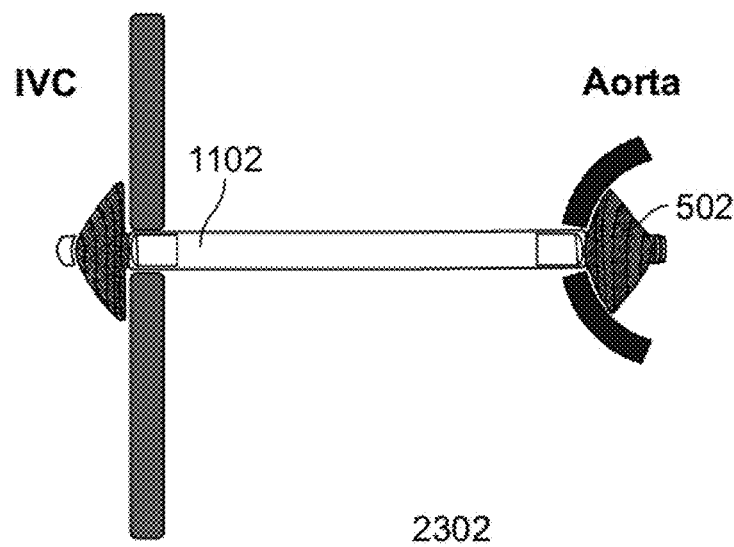
FIG. 22 is a schematic of the treatment method of FIG. 21, showing the scaling structures of the shunt being capable of conforming to different curvature of the aorta and the vena cava, according to an embodiment herein.
Figure 23:
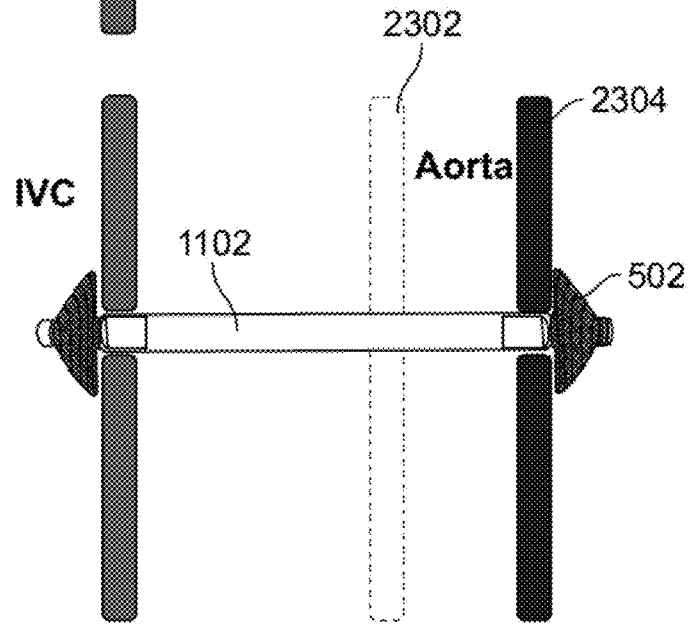
FIG. 23 is a schematic of the treatment method of FIG. 21, showing that the main body of the shunt (of FIG. 8) is configured to expand to maintain a fluid seal around the arterial puncture site, according to an embodiment herein.

In some embodiments, the shunt, the proximal sealing structure, and/or the distal scaling structure are composed of a deformable material capable of conforming to varying curvature and shape of the aorta and/or the vein (FIGS. 22-23). In some embodiments, the shunt body 818 comprises a flexible, compliant stretchy tube that can lengthen as the aneurysmal sac shrinks, and as the distance between the puncture sites of the aorta and vena cava increases. In some embodiments, the shunt body 818 can stretch from about 1% to about 300% of its original length. In some embodiments, the shunt body 818 can compress from about 100% to about 25% of its original length.

Figure 24:
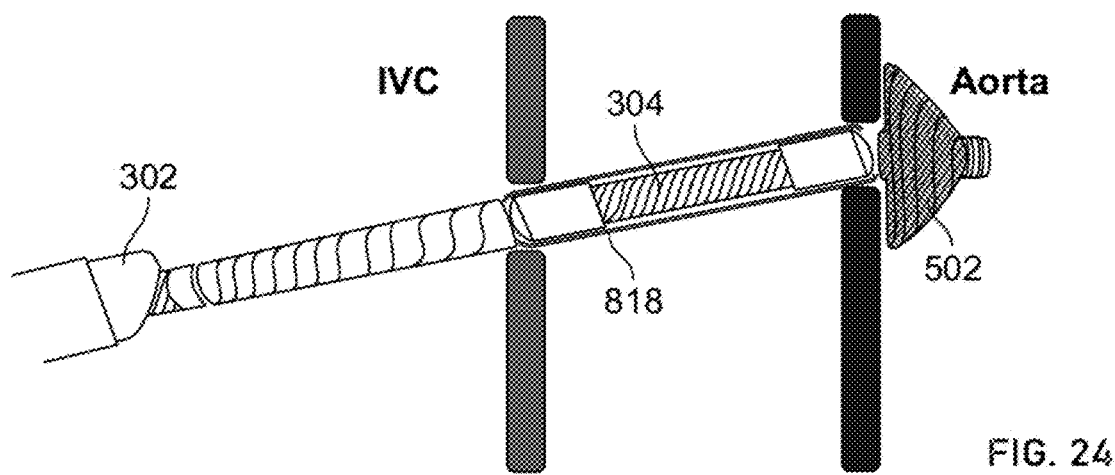
FIG. 24 is a schematic drawing showing the stent-like sealing structures of the shunt being pivotable relative to the main body of the shunt (from FIG. 8), according to an embodiment herein.

In some embodiments, the shunt and the sealing structures (e.g., distal 502, proximal 504) are configured to be pivotably connected (FIG. 24) to the vascular (e.g., arterial 814, venous 812 puncture sites). For example, in some embodiments, the sealing structures on both ends are pivotable relative to the shunt body 818, allowing for a fluid tight seal regardless of puncture angle. In some embodiments, the sealing structures comprise of a braided or laser cut metal such as nitinol or steel, a bioabsorbable material, a polymer, a compliant balloon, or any variant thereof. In some embodiments, the sealing structures are configured to compress from about 100% to about 25% of their original length. In some embodiments, the sealing structures are identical in shape, size, and/or material to each other. In some embodiments, the arterial puncture site sealing structure is not identical in shape, size, and/or material as the venous puncture site sealing structure, to account for differences in mechanical and fluid properties found between the vein and the artery.

The shunt implantation as described in FIGS. 8-24 may be implemented for any location of an aneurysm. In some cases, the puncture site for the aorta may be located upstream (e.g., superior) of the aneurysmal sac (with respect to blood flow therethrough).

Implantation Using Snare Wire

Figure 25:
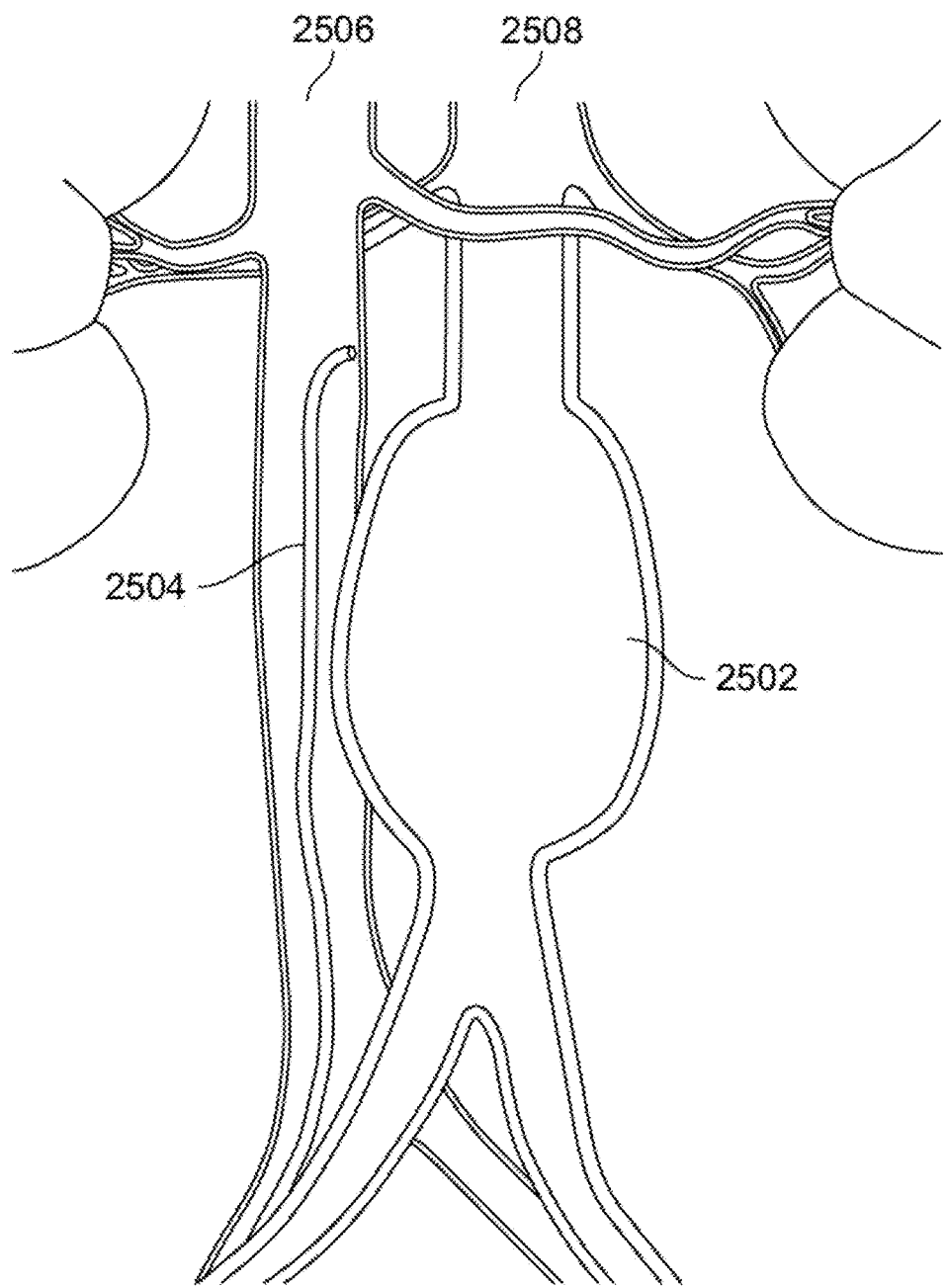
FIG. 25 is a schematic drawing showing another treatment method of an abdominal aortic aneurysm, wherein a distal end of an access catheter is positioned near a venous puncture site, according an embodiment described herein.
Figure 26:
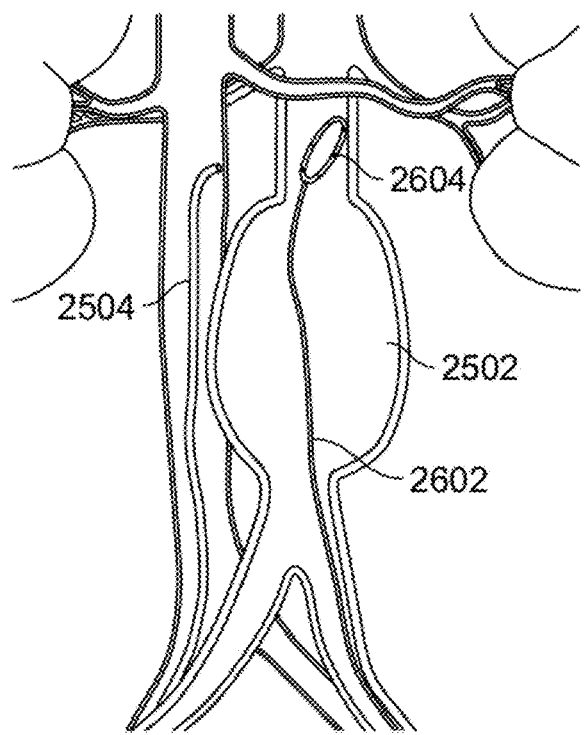
FIG. 26 is a schematic showing the treatment method of FIG. 25, wherein a snare wire is advanced through the aorta and aneurysm sac, such that a snare wire loop is disposed proximate to a targeted arterial puncture site, according an embodiment herein.

In some embodiments, a shunt may be implanted using a snare wire, as depicted, for example in FIGS. 25-35. In some embodiments, a steerable catheter 2504 is inserted through the vena cava (FIG. 25). In some cases, the catheter 2504 is advanced to a puncture site at the vena cava using a similar method as described herein for FIGS. 8-24. In some embodiments, a snare wire 2602 is advanced through the artery (FIG. 26), through the aneurysm sac 2502, and to a location proximate to a targeted puncture site of the aorta. In some embodiments, the targeted puncture site of the artery is disposed upstream (e.g., with respect to blood flow) of the aneurysmal sac 2502.

In some embodiments, the snare wire 2602 includes a proximal end and a distal end. In some embodiments, the snare wire has a length of from about 10 cm to about 100 cm. In some embodiments, the snare wire has a thickness of from about 0.1 mm to about 3 mm.

In some embodiments, the snare wire 2602 includes a snare wire loop 2604 disposed at the distal end of the snare wire. In some embodiments, the snare wire loop 2604 is configured to be tightened and/or loosened. In some embodiments, tightening the snare wire loop decreases the snare wire loop diameter.

Figure 27:
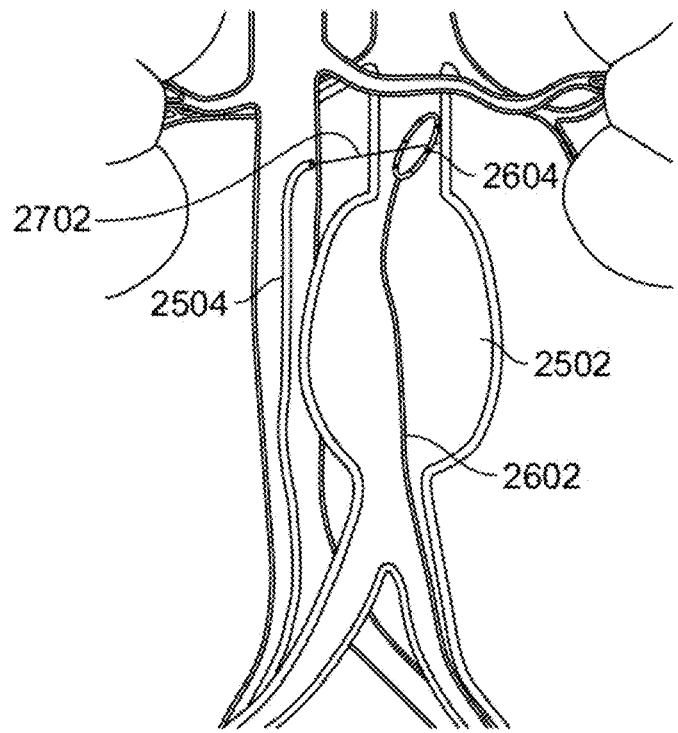
FIG. 27 is a schematic of the treatment method from FIG. 26, depicting transcaval penetration of a guidewire from the catheter to within the snare wire loop, according to an embodiment herein.
Figure 28:
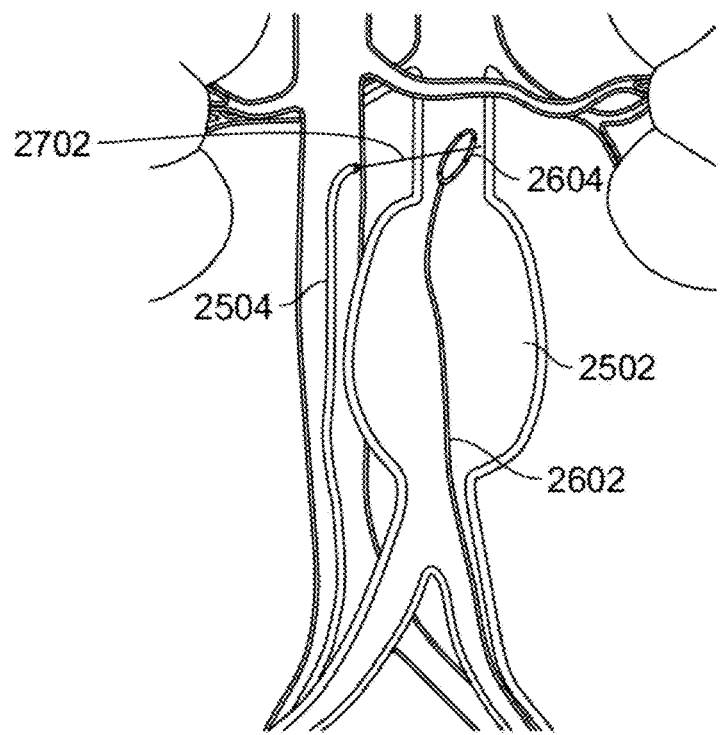
FIG. 28 is a schematic of the treatment method from FIG. 27, depicting the snare wire being tightened such that the snare wire loop diameter is reduced.
Figure 29:
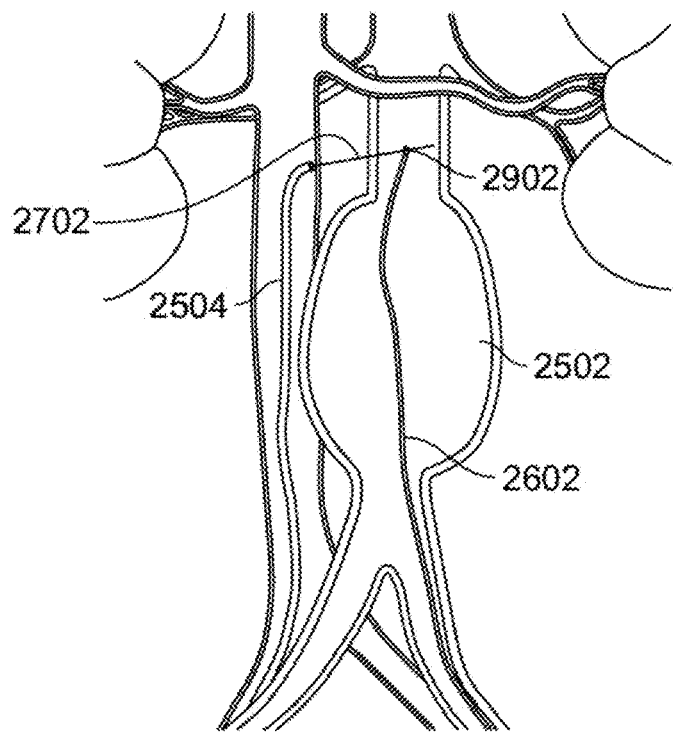
FIG. 29 is a schematic of the treatment method from FIG. 28, depicting the snare wire being tightened such that the snare wire is secured to the guidewire.
Figure 30:
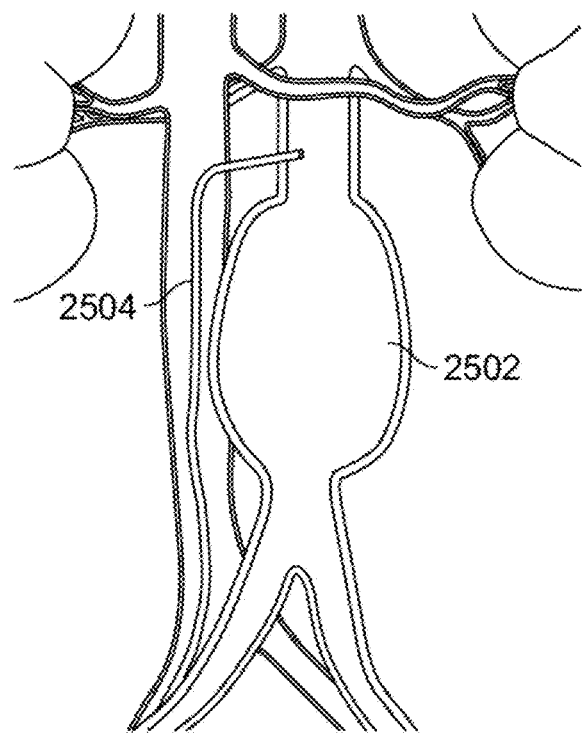
FIG. 30 is a schematic of the treatment method from FIG. 29, depicting transcaval penetration of the access catheter from the vena cava to the aorta, according to an embodiment herein.
Figure 31:
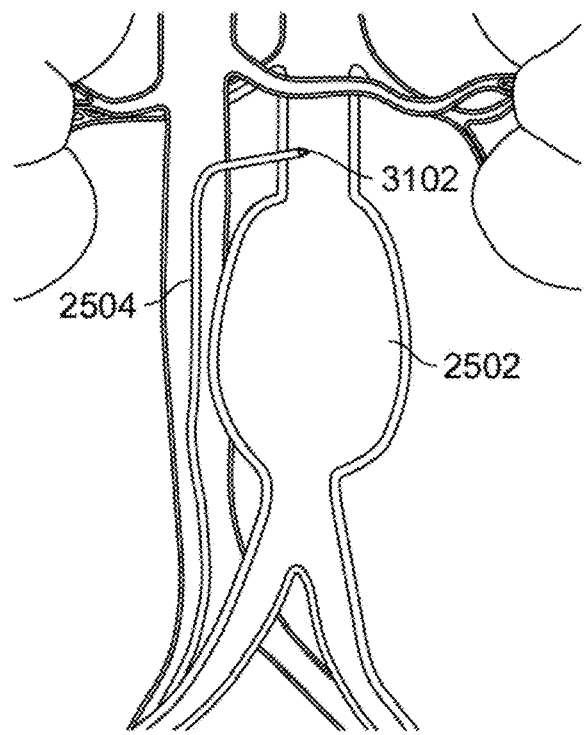
FIG. 31 is a schematic of the treatment method from FIG. 30, depicting the access catheter disposed within the aorta with a shunt being advanced to the aorta, according to an embodiment herein.
Figure 32:
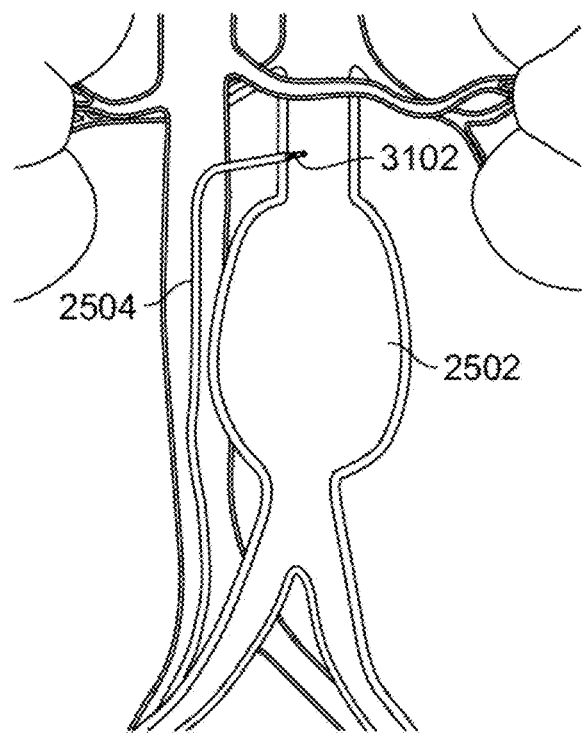
FIG. 32 is a schematic of the treatment method from FIG. 31, depicting a shunt extending from the access catheter, according to an embodiment herein.
Figure 33:
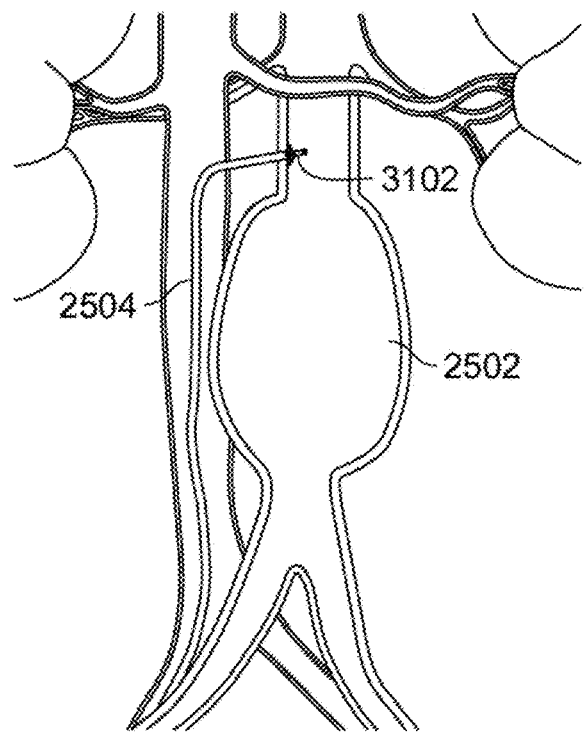
FIG. 33 is a schematic of the treatment method from FIG. 32, depicting the access catheter being withdrawn from the aorta and a sealing structure of the shunt being deployed, according to an embodiment herein.
Figure 34:
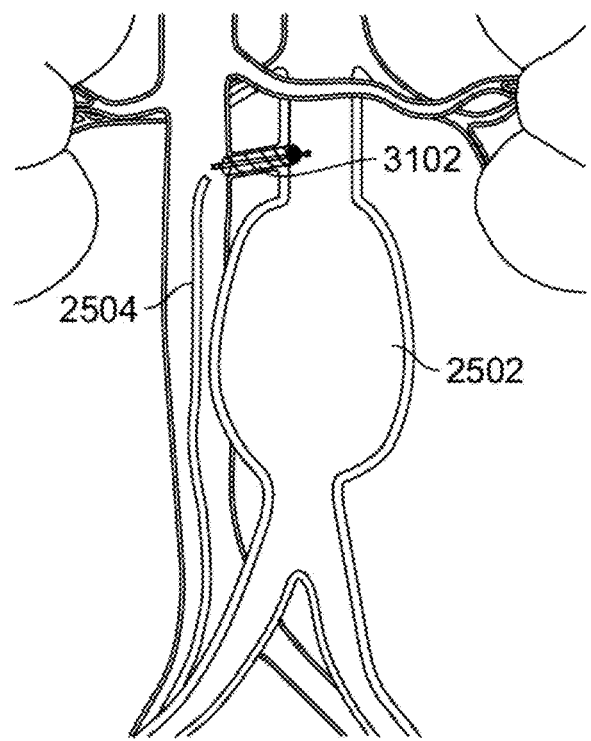
FIG. 34 is a schematic of the treatment method from FIG. 33, depicting both shunt sealing structures deployed, and the catheter withdrawn from the shunt lumen, according to an embodiment herein.
Figure 35:
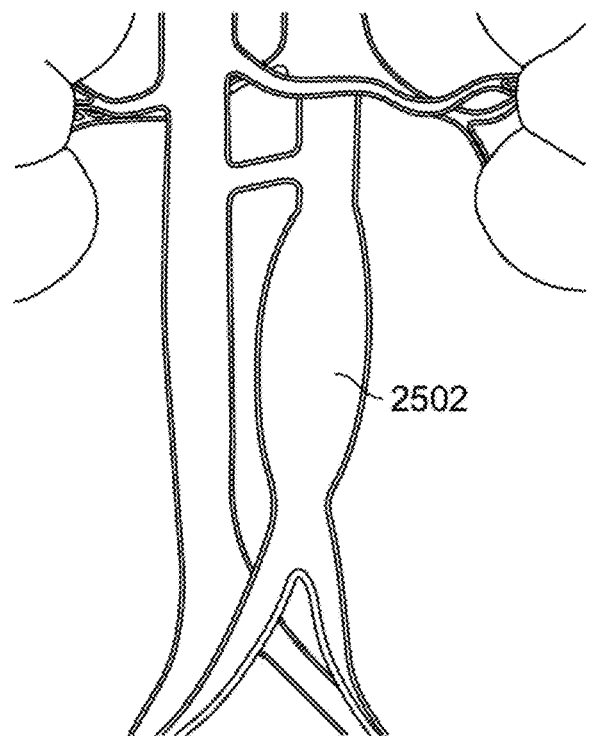
FIG. 35 is a schematic of the treatment method from FIG. 34, depicting shunt lumen bridging the vena cava and aorta, according to an embodiment herein.

In some embodiments, a guidewire 2702 is then advanced from the catheter 2504 to puncture through the vena cava and access the aorta via the puncture site at the aorta (FIG. 27). In some embodiments, the guidewire 2702 is advanced until it is located within the snare wire loop 2604. In some embodiments, radiopaque markers on the guidewire 2702 and/or the snare wire 2602 (e.g., snare wire loop) are used to determine the location of the guidewire relative to the snare wire loop. In some embodiments, the snare wire is tightened, so as to shorten the snare wire loop (FIG. 28), and secure it about the guidewire, thereby securing the snare wire to the guidewire (FIG. 29). In some embodiments, the snare wire is then pulled, so as to advance the catheter 2504 through the aorta puncture site (FIG. 30). In some embodiments, the guidewire, is then cut and removed. In some embodiments, a shunt 3102 is then advanced through the catheter to the aorta (FIGS. 31-32). In some embodiments, a distal sealing structure is then deployed (FIG. 33), so as to seal the arterial puncture site. In some embodiments, the distal sealing structure is deployed similar to as described herein for the distal sealing structure 502, using a sliding sheath. Accordingly, withdrawing the catheter and a corresponding sliding sheath enables a proximal sliding structure for the shunt 3102 to be deployed, thereby providing a sealed fluid (e.g., blow) flow path between the aorta and vena cava.

Bypass Graft

Figure 36:
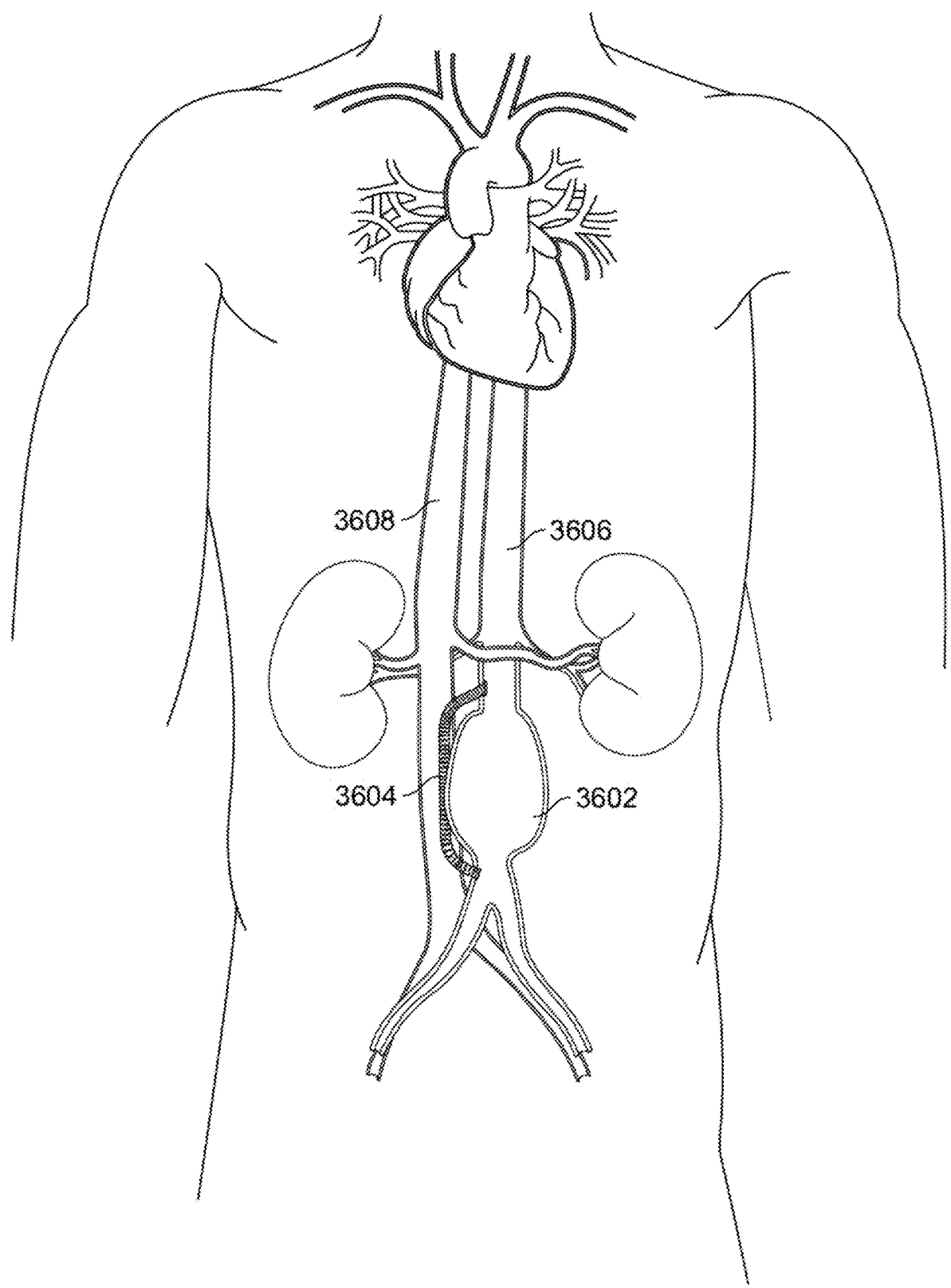
FIG. 36 is a schematic of another treatment of an aortic aneurysm, depicting a bypass graft implanted around the aneurysm sac, according to an embodiment herein.

As described herein, in some aspects, systems and methods disclose treating an aortic aneurysm by implanting a bypass graft so as to divert some or all of the fluid (e.g., blood) flow around an aneurysmal sac, thereby alleviating the pressure against the aneurysmal sac, and reducing the risk of an aneurysm rupture. FIG. 36 depicts an exemplary bypass graft 3604 implanted into a subject. In some embodiments, the bypass graft 3604 accesses the aorta 3606 through an arterial puncture site. In some embodiments, the bypass graft 3604 passes within a vena cava 3608, and then rejoins the aorta downstream of an aneurysm sac 3602. In some embodiments, the system includes one or more (e.g., 1, 2, 3, 4, 5, 6, 7, 8, 9, or 10) bypass grafts. In some embodiments, the bypass graft includes a proximal end, a distal end, and a bypass graft lumen traversing the length of the bypass graft from the proximal end to the distal end. In some embodiments, the bypass graft 3604 has a length of from about 20 mm to about 20 cm. In some embodiments, the bypass graft has a bypass graft wall forming a bypass graft inner diameter and a bypass graft outer diameter. In some embodiments, the bypass graft inner diameter is from about 5 mm to about 30 mm. In some embodiments, the bypass graft outer diameter is from about 5 mm to about 30 mm.

In some embodiments, the bypass graft 3604 comprises of material including expanded polytetrafluoroethylene (e-PTFE), or woven, knitted, or velour design polyethylene terephthalate (PET) or Dacron. The bypass graft 3604 may be manufactured from any biologically acceptable material that possesses the ability to be shaped into a tubular structure having the required compliance. Polymeric fibers may be employed, such as polyurethanes, polyethylene terephthalate, polypropylene, and polytetrafluoroethylene, and good results may be obtained through the use of wires of such metals as stainless steel and cobalt-chromium alloys. Polymeric fibers may be elastomeric polymers, e.g. polyurethane elastomers or composite fibers that act in an elastic fashion. Polymeric fibers may be "shrinking" polymers, where the shrinkage may be controllable, e.g., pressure-sensitive polymers. Wires made of shape memory alloys such as Nitinol may be used to advantage. The bypass graft 3604 may be at least partially coated with a polymer for improved biocompatibility.

Figure 37:
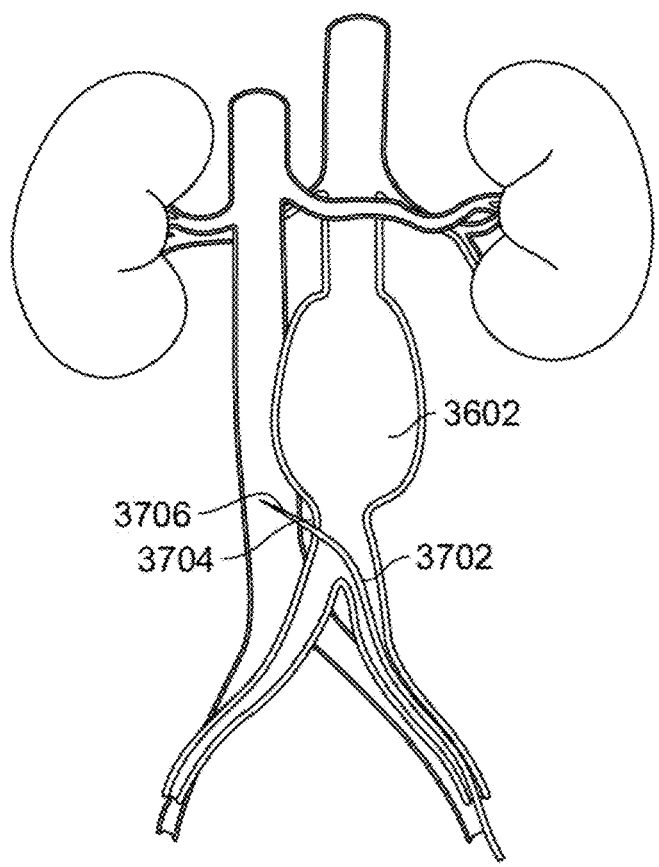
FIG. 37 is a schematic of the treatment method from FIG. 36, depicting an access catheter advancing through an artery, a first arterial puncture site, a first venous arterial puncture site, and into a vena cava, according to an embodiment herein.
Figure 38:
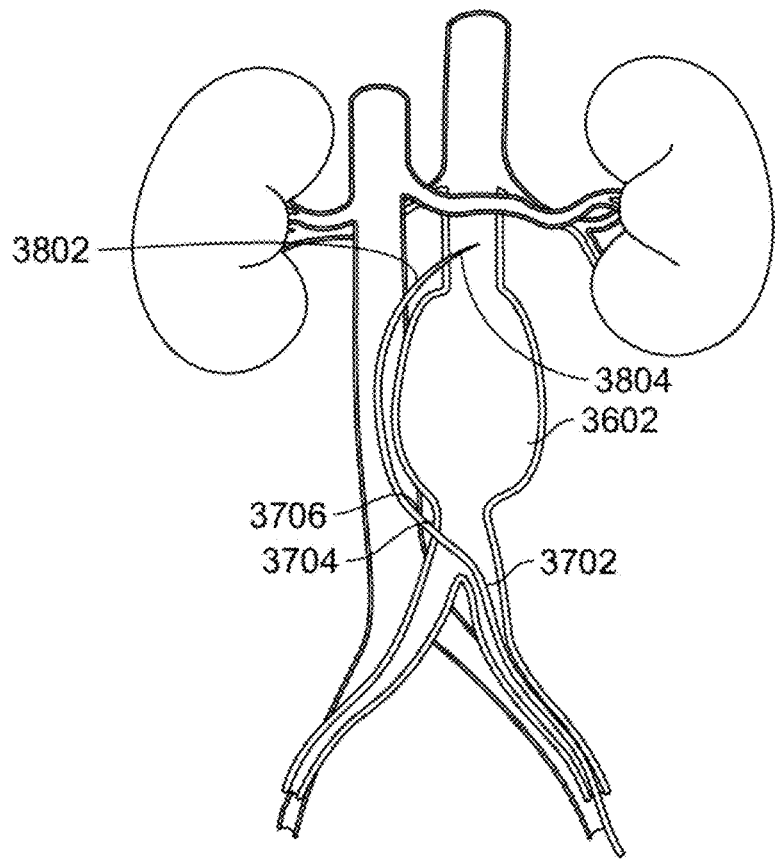
FIG. 38 is a schematic of the treatment method from FIG. 37, depicting the catheter advancing to the artery passing through a second venous and arterial puncture site, according to an embodiment herein.
Figure 39:
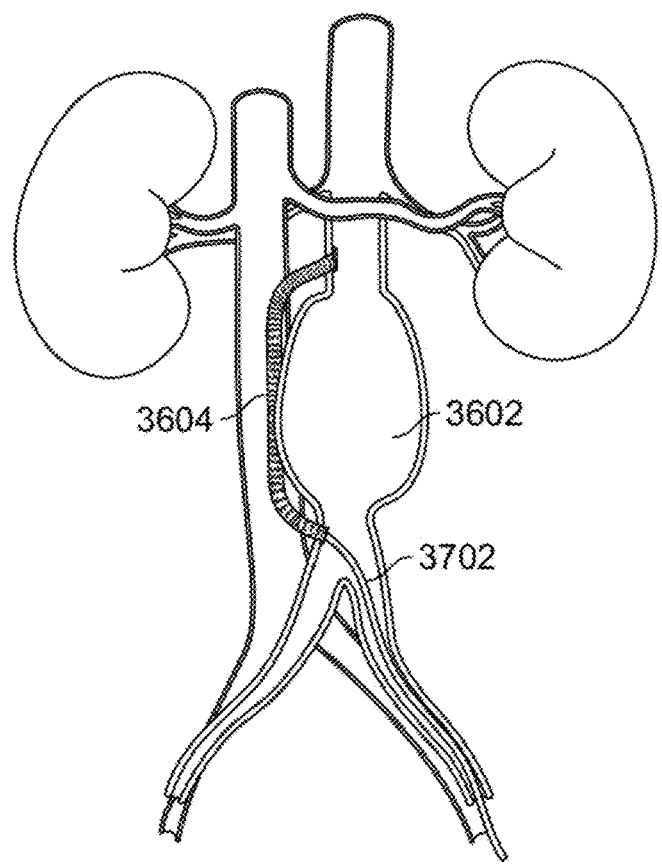
FIG. 39 is a schematic of the treatment method from FIG. 38, depicting a graft being advanced across the first and second venous and arterial puncture sites, according to an embodiment herein.
Figure 40:
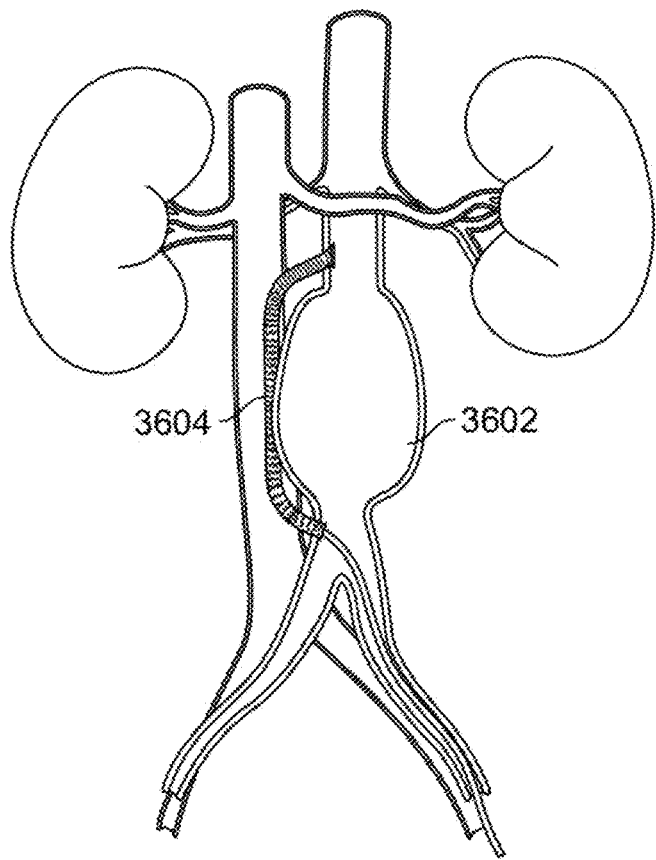
FIG. 40 is a schematic of the treatment method from FIG. 39, depicting a graft being secured to the first and second arterial puncture sites, thereby providing a flow path for the blood that bypasses the aneurysm sac, according to an embodiment herein.

In some embodiments, implanting a bypass graft includes introducing a catheter 3702, as herein described, into an artery (e.g., femoral artery) of a subject. In some embodiments, after introducing the catheter into the artery, the method includes navigating the catheter 3702 within the artery to a first arterial puncture site 3704 disposed substantially near a first venous puncture site 3706 (FIG. 37). In some embodiments, the catheter 3702 is then advanced through the first arterial puncture site 3704 and through the first venous puncture site 3706 and into the femoral vein (e.g., vena cava). In some embodiments, the catheter 3702 is then advanced to a second venous puncture site 3802 and through a second arterial puncture site 3804 (FIG. 38). In some embodiments, the aneurysm sac 3602 is located between the first and second arterial puncture sites. In some embodiments, the first and second venous and arterial puncture sites are penetrated by a guidewire before the catheter is driven through each puncture site. In some embodiments, a graft is then advanced via the catheter through the first arterial puncture site 3704, the first and second venous puncture sites 3706, 3802, and the second arterial puncture site 3804. In some embodiments, a sealing structure is deployed at the first and second arterial puncture sites, thereby sealing fluid (e.g., blood) to flow through the graft and not pass into the vena cava. In some embodiments, the sealing structures are similar to the distal sealing structure 502 and proximal sealing structure 504 described herein. Accordingly, in some embodiments, fluid is able to flow through both the bypass graft and the aneurysm sac, whereas such reduction in pressure and/or flow through the aneurysm sac will alleviate the tension imposed thereto.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. Provide herein are embodiments in which exactly one member of the group is present in, employed in, or otherwise relevant to a given product or process. Provided herein are embodiments in which more than one, or all of the group members are present in, employed in, or otherwise relevant to a given product or process.

Furthermore, the inventions provided herein encompass all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the inventions provided and described herein, or aspects of the inventions described and provided herein, is/are referred to as comprising particular elements and/or features, certain embodiments of the inventions or aspects of the inventions consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the inventions described and provided herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment that falls within the prior art may be explicitly excluded from any one or more of the claims. Because such embodiments are deemed to be known to one of ordinary skill in the art, they may be excluded even if the exclusion is not set forth explicitly herein. Any particular embodiment can be excluded from any claim, for any reason, whether or not related to the existence of prior art.

Each numerical value presented herein is contemplated to represent a minimum value or a maximum value in a range for a corresponding parameter. Accordingly, when added to the claims, the numerical value provides express support for claiming the range, which may lie above or below the numerical value, in accordance with the teachings herein. Every value between the minimum value and the maximum value within each numerical range presented herein (including any minimum, nominal, and maximum values shown in any tables), is contemplated and expressly supported herein, subject to the number of significant digits expressed in each particular range. The application expressly contemplates the ranges between the minimum and nominal values, nominal and maximum values, and minimum and maximum values.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present inventions, as defined in the following claims.

What is claimed is:

1. A method of treating an aortic aneurysm in a subject, the method comprising:
   puncturing an artery to define to define an arterial puncture site;
   after puncturing the artery, delivering an endograft to the aortic aneurysm;
   advancing a shunt through a venous puncture site of a vein to access the arterial puncture site of the artery, the arterial puncture site disposed within the aortic aneurysm or upstream of the aortic aneurysm; and
   securing the shunt to the artery and vein by deploying i) an arterial sealing structure coupled to a distal end of the shunt, and ii) deploying a venous sealing structure coupled to a proximal end of the shunt, thereby enabling fluid to flow from the artery to the vein.

2. The method of claim 1, wherein advancing the shunt occurs contemporaneous or substantially contemporaneous with the delivering the endograft within the aortic aneurysm.

3. The method of claim 1, further comprising:
   prior to securing the shunt:
   puncturing the vein to define the venous puncture site.

4. The method of claim 3, wherein the puncturing of the vein and the puncturing of the artery includes moving a guidewire through the venous puncture site and the arterial puncture site.

5. The method of claim 4, further comprising:
dilating the venous puncture site and the arterial puncture site to a diameter corresponding to a diameter of the shunt when the shunt is in a delivery configuration prior to the deploying the arterial sealing structuring and the venous sealing structure.

6. The method of claim 1, wherein advancing the shunt occurs after the delivering the endograft within the aortic aneurysm.

7. The method of claim 1, wherein advancing the shunt comprises:
inserting a catheter within the vein, the catheter being steerable via a catheter handle coupled thereto; and
extending a sliding sheath from the catheter, the sliding sheath detachably coupled to the shunt.

8. The method of claim 1, wherein securing one or both of the arterial sealing structure and the venous sealing structure comprises withdrawing the sliding sheath away from the artery.

9. The method of claim 1, wherein one or both of the arterial sealing structure and the venous sealing structure are self-expandable.

10. The method of claim 1, wherein the aortic aneurysm is an abdominal aortic aneurysm.

11. The method of claim 1, wherein one or both of the arterial and venous sealing structures are pivotally attached to the shunt.

12. The method of claim 1, wherein the shunt comprises a shunt body made of a compliant material capable of stretching and shrinking.

13. The method of claim 12, wherein the shunt body comprises a lumen therein so as to enable the fluid to flow from the artery to the vein.

14. The method of claim 1, further comprising:
after the securing the shunt to the artery and vein, resizing a diameter of at least a portion of the shunt to modify an amount of blood flow therethrough.

15. The method of claim 1, wherein the method of treating the aortic aneurysm is a method of treating an endoleak associated with the endograft implanted within the aortic aneurysm, and the securing the shunt to the artery and vein enables blood flow from the endoleak through a lumen defined by the shunt from the artery to the vein.

16. A method of treating an aortic aneurysm in a subject, the method comprising:
contemporaneous or substantially contemporaneous with implantation of an endograft within the aortic aneurysm, advancing a shunt through a venous puncture site of a vein to access an arterial puncture site of an artery, the arterial puncture site disposed within the aortic aneurysm or upstream of the aortic aneurysm; and
securing the shunt to the artery and vein by deploying i) an arterial sealing structure coupled to a distal end of the shunt, and ii) deploying a venous sealing structure coupled to a proximal end of the shunt, thereby enabling fluid to flow from the artery to the vein.

17. The method of claim 16, wherein one or both of the arterial sealing structure or the venous sealing structure are self-expandable.

18. The method of claim 16, wherein the aortic aneurysm is an abdominal aortic aneurysm.

19. The method of claim 16, further comprising:
dilating the venous puncture site and the arterial puncture site to a diameter corresponding to a diameter of the shunt when the shunt is in a delivery configuration prior to the deploying the arterial sealing structuring and the venous sealing structure.

20. A method of treating an aortic aneurysm in a subject having an endograft implanted within the aortic aneurysm, the method comprising:
advancing a shunt through a venous puncture site of a vein to access an arterial puncture site of an artery, the arterial puncture site disposed (1) within the aortic aneurysm or upstream of the aortic aneurysm and (2) adjacent the endograft or upstream of the endograft; and
securing the shunt to the artery and vein by deploying i) an arterial sealing structure coupled to a distal end of the shunt, and ii) deploying a venous sealing structure coupled to a proximal end of the shunt, thereby enabling fluid to flow from the artery to the vein.

21. The method of claim 20, wherein the method of treating the aortic aneurysm is a method of treating an endoleak associated with the endograft implanted within the aortic aneurysm.

22. The method of claim 20, wherein one or both of the arterial sealing structure or the venous sealing structure are self-expandable.

23. The method of claim 20, wherein the aortic aneurysm is an abdominal aortic aneurysm.

24. A method of treating an aortic aneurysm in a subject, the method comprising:
advancing a shunt through a venous puncture site of a vein to access an arterial puncture site of an artery, the arterial puncture site disposed within the aortic aneurysm or upstream of the aortic aneurysm;
delivering an endograft to the aortic aneurysm; and
after delivering the endograft, securing the shunt to the artery and vein by deploying i) an arterial sealing structure coupled to a distal end of the shunt, and ii) deploying a venous sealing structure coupled to a proximal end of the shunt, thereby enabling fluid to flow from the artery to the vein.

25. The method of claim 24, wherein one or both of the arterial sealing structure or the venous sealing structure are self-expandable.

26. The method of claim 24, wherein the aortic aneurysm is an abdominal aortic aneurysm.

27. A method of treating an aortic aneurysm in a subject, comprising:
puncturing a vein to define a venous puncture site;
puncturing an artery via the venous puncture site to define an arterial puncture site;
after the puncturing the artery, delivering an endograft to the aortic aneurysm; and
after the puncturing the artery, delivering a shunt including a venous sealing structure and an arterial sealing structure such that the venous sealing structure is disposed within the vein and the arterial sealing structure is disposed within the artery.

28. The method of claim 27, wherein one or both of the arterial sealing structure or the venous sealing structure are self-expandable.

29. The method of claim 27, wherein the aortic aneurysm is an abdominal aortic aneurysm.

30. The method of claim 20, wherein the arterial puncture site is disposed within the aortic aneurysm and adjacent the endograft.

* * * * *